(12) United States Patent
Benson et al.

(10) Patent No.: US 9,848,814 B2
(45) Date of Patent: Dec. 26, 2017

(54) VEHICLE SEAT WITH INTEGRATED SENSORS

(71) Applicant: FAURECIA AUTOMOTICE SEATING, LLC., Troy, MI (US)

(72) Inventors: Matthew K. Benson, Holland, MI (US); Dana R. Lowell, Holland, MI (US); Sean M. Montgomery, Astoria, NY (US); Brian R. Dexter, Grand Haven, MI (US); Jeffery T. Bonk, Chesterfield, MI (US); David L. Cummings, Jackson Heights, NY (US); Alexander S. Haase, Ypsilanti, NY (US); Samuel Baudu, Boulogne Billancourt (FR); Radouane Boussetta, Issy les Moulineaux (FR); Pioter Drubetskoy, Bronx, NY (US); Anne-Isabelle Dacosta-Mallet, Etrechy (FR); Claire Mitchell, Brooklyn, NY (US)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 0 days.

(21) Appl. No.: 15/116,952

(22) PCT Filed: Feb. 20, 2015

(86) PCT No.: PCT/US2015/016803
§ 371 (c)(1),
(2) Date: Aug. 5, 2016

(87) PCT Pub. No.: WO2015/127193
PCT Pub. Date: Aug. 27, 2015

(65) Prior Publication Data
US 2016/0354027 A1  Dec. 8, 2016

Related U.S. Application Data

(60) Provisional application No. 61/942,543, filed on Feb. 20, 2014, provisional application No. 61/942,513, (Continued)

(51) Int. Cl.
*G06F 7/00* (2006.01)
*A61B 5/18* (2006.01)
(Continued)

(52) U.S. Cl.
CPC .............. *A61B 5/18* (2013.01); *A61B 5/0022* (2013.01); *A61B 5/0205* (2013.01);
(Continued)

(58) Field of Classification Search
None
See application file for complete search history.

(56) References Cited

U.S. PATENT DOCUMENTS 5,069,214 A   12/1991 Samaras
7,206,631 B2   4/2007 Kawachi
(Continued)

FOREIGN PATENT DOCUMENTS

CN   0104875744   9/2015
DE   102005038289   3/2007
(Continued)

OTHER PUBLICATIONS

PCT Search Report and Written Opinion completed by the ISA/EP dated May 21, 2015 and issued in connection with PCT/US2015/016803.
(Continued)

*Primary Examiner* — Brent Swarthout
(74) *Attorney, Agent, or Firm* — Barnes & Thornburg LLP

(57) ABSTRACT

An occupant support system includes a vehicle seat and an electronics system for the vehicle seat. The electronics system includes a sensor system configured to obtain sensor data and a computer coupled to the sensor system to process the sensor data and perform a predetermined action using the sensor data.

23 Claims, 27 Drawing Sheets

Related U.S. Application Data filed on Feb. 20, 2014, provisional application No. 61/942,493, filed on Feb. 20, 2014.

(51) Int. Cl.

| | | |
|---|---|---|
| *A61B 5/00* | (2006.01) | |
| *A61B 5/024* | (2006.01) | |
| *A61B 5/0432* | (2006.01) | |
| *A61B 5/053* | (2006.01) | |
| *A61B 5/11* | (2006.01) | |
| *B60N 2/00* | (2006.01) | |
| *A61B 5/0205* | (2006.01) | |
| *A61B 5/0295* | (2006.01) | |
| *A61B 5/0402* | (2006.01) | |
| *A61B 5/16* | (2006.01) | |
| *A61M 21/02* | (2006.01) | |
| *B60N 2/02* | (2006.01) | |
| *B60N 2/44* | (2006.01) | |
| *B60N 2/56* | (2006.01) | |
| *A61B 5/021* | (2006.01) | |
| *A61B 5/117* | (2016.01) | |
| *A61B 5/08* | (2006.01) | |
| *A61B 5/1455* | (2006.01) | |
| *A61M 21/00* | (2006.01) | |

(52) U.S. Cl.
CPC ........ *A61B 5/0295* (2013.01); *A61B 5/02405* (2013.01); *A61B 5/0402* (2013.01); *A61B 5/0432* (2013.01); *A61B 5/0533* (2013.01); *A61B 5/1102* (2013.01); *A61B 5/165* (2013.01); *A61B 5/6893* (2013.01); *A61B 5/7221* (2013.01); *A61B 5/7275* (2013.01); *A61B 5/7282* (2013.01); *A61M 21/02* (2013.01); *B60N 2/002* (2013.01); *B60N 2/0244* (2013.01); *B60N 2/448* (2013.01); *B60N 2/5678* (2013.01); *A61B 5/02125* (2013.01); *A61B 5/0816* (2013.01); *A61B 5/117* (2013.01); *A61B 5/14552* (2013.01); *A61M 2021/0022* (2013.01); *A61M 2021/0066* (2013.01); *A61M 2205/3303* (2013.01); *B60N 2002/0268* (2013.01)

(56) References Cited

U.S. PATENT DOCUMENTS

| | | |
|---|---|---|
| 7,239,945 B2 | 7/2007 | Hiemer |
| 7,774,052 B2 | 8/2010 | Burton |
| 8,430,817 B1 * | 4/2013 | Al-Ali et al. ................ 600/301 |
| 8,616,654 B2 | 12/2013 | Zenk |
| 9,475,389 B1 | 10/2016 | Fung |
| 2006/0068693 A1 | 3/2006 | Kono |
| 2010/0185068 A1 | 7/2010 | Park |
| 2011/0015468 A1 * | 1/2011 | Aarts ................... A61B 5/0205 600/26 |
| 2012/0078123 A1 | 3/2012 | Futatsuyama et al. |
| 2013/0070043 A1 | 3/2013 | Geva et al. |
| 2014/0039330 A1 | 2/2014 | Sec Sang Man et al. |
| 2014/0240132 A1 * | 8/2014 | Bychkov ................. A61B 5/18 340/576 |
| 2014/0276112 A1 | 9/2014 | Fung |
| 2015/0313475 A1 * | 11/2015 | Benson ................ A61B 5/6893 297/217.3 |
| 2016/0001781 A1 | 1/2016 | Fung |
| 2016/0029940 A1 | 2/2016 | Iizuka |
| 2017/0158202 A1 | 6/2017 | Yang |

FOREIGN PATENT DOCUMENTS

| | | |
|---|---|---|
| DE | 102007053119 | 5/2009 |
| DE | 102009021532 | 11/2010 |
| JP | 2010264092 | 11/2010 |
| KR | 1020010061858 | 7/2001 |
| KR | 1020140027641 | 3/2014 |
| KR | 0101642697 | 8/2016 |
| WO | 20130109154 A1 | 7/2013 |
| WO | 2014147828 | 9/2014 |
| WO | 2015200224 | 12/2015 |

OTHER PUBLICATIONS

Chinese Office Action for Chinese App. No. 201380064313.2 dated Apr. 12, 2017, 3376 CN II, 21 pages.

PCT International Search Report and Written Opinion completed by the ISA/US dated Apr. 22, 2014 and issued in connection with PCT/US2013/071620.

Chinese Office Action for Chinese App. No. 201380064313.2 sent on Sep. 28, 2017, 3376 CN II, 19 pages.

\* cited by examiner

| Pulse Ox Sensor | Description | Manufacturer | Part Number |
|---|---|---|---|
| | PHOTODIODE PIN HI SPEED HI SENS w DL Filter | | VBPW34FAS |
| | OPA2277 | TI | OPA2277UA |
| | 10K Res | Yageo | RC0603FR-0710KL |
| | 100K Res | Yageo | RC0603FR-07100KL |
| | 0.47nF Cap | TDK | C1608C0G1H471F |
| | 1050nm LED | Epitex | SMT1050 |
| | 950nm LED | Vishay | VSMS3700-GS08 |
| | 850nm LED | Vishay | VSMY3850-GS08 |
| | 830nm LED | Vishay | VSMG2700-GS08 |
| | 810nm LED | Epitex | SMT810N |
| | Inverter Logic Gate | | SN74LVC1GU04DCKR |
| | AND Gate | | SN74LVC1G08DCKR |
| | MIC4812 | Micrel | MIC4812YMME |
| | 8.45K SET Res | Vishay | CRCW06038K45FKEA |
| | 200K Res | Vishay | CRCW0603200KFKEA |
| | 2.2uF Cap | Murata | GRM188R60J225KE19D |
| | 22uF Cap | TDK | C1608X5R0J226M |
| | 0.1uF Cap | Murata | GRM188R71C104KA01D |
| | CONN RCPT 7POS 1.25MM R/A SMD | Molex | 5023860770 |
| | CONN RCPT 7POS 1.25MM W/B VERT | Molex | 5023820770 |
| | CONN PLUG HSNG 7POS 1.25MM WTB | Molex | 5023800700 |
| | PLUG TERM 1.25 26-28AWG TIN | Molex | 5023810000 |
| Pulse Ox Extras | 8.25K Res | | CRCW06038K25FKEA |
| | PHOTODIODE PIN HI SPEED HI SENS w/o DL Filter | | VBPW34S |
| | 0603 Resistor Kit | | PHG2A-KIT |
| | 0603 Cap Kit 10pF-0.1uF | | S-0603-DIGI |
| | OR gate | TI | SN74LVC1G32DCKR |

FIG. 19

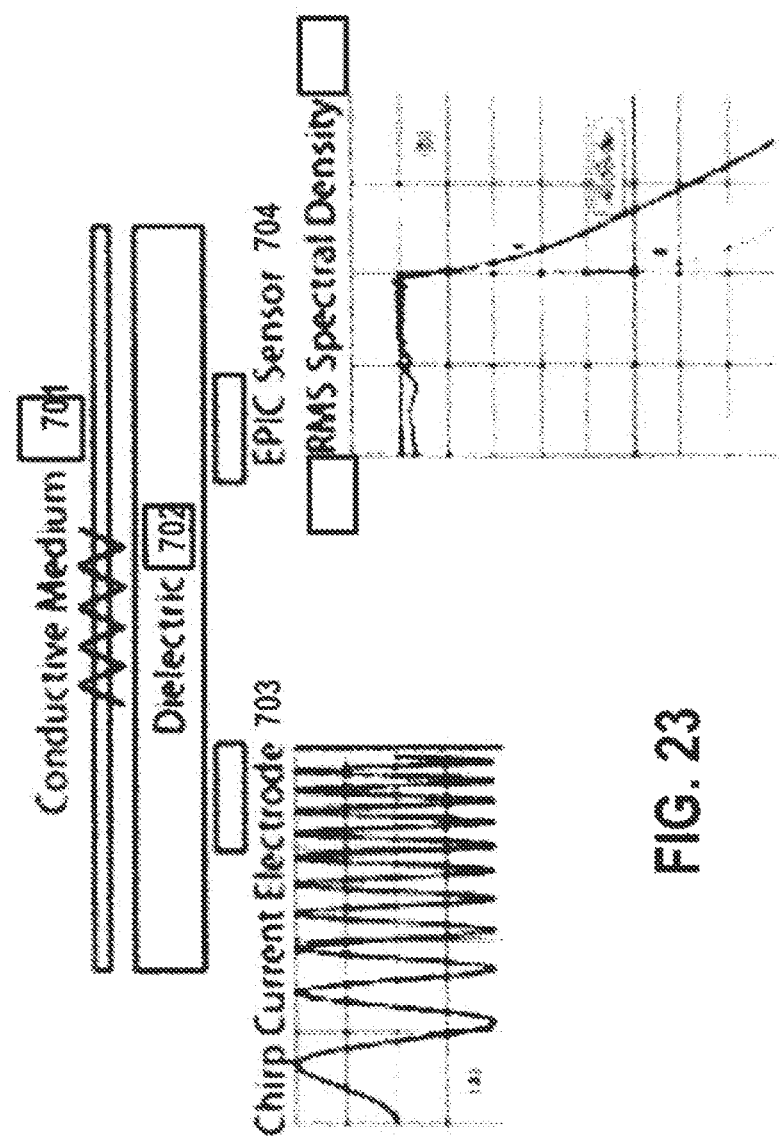

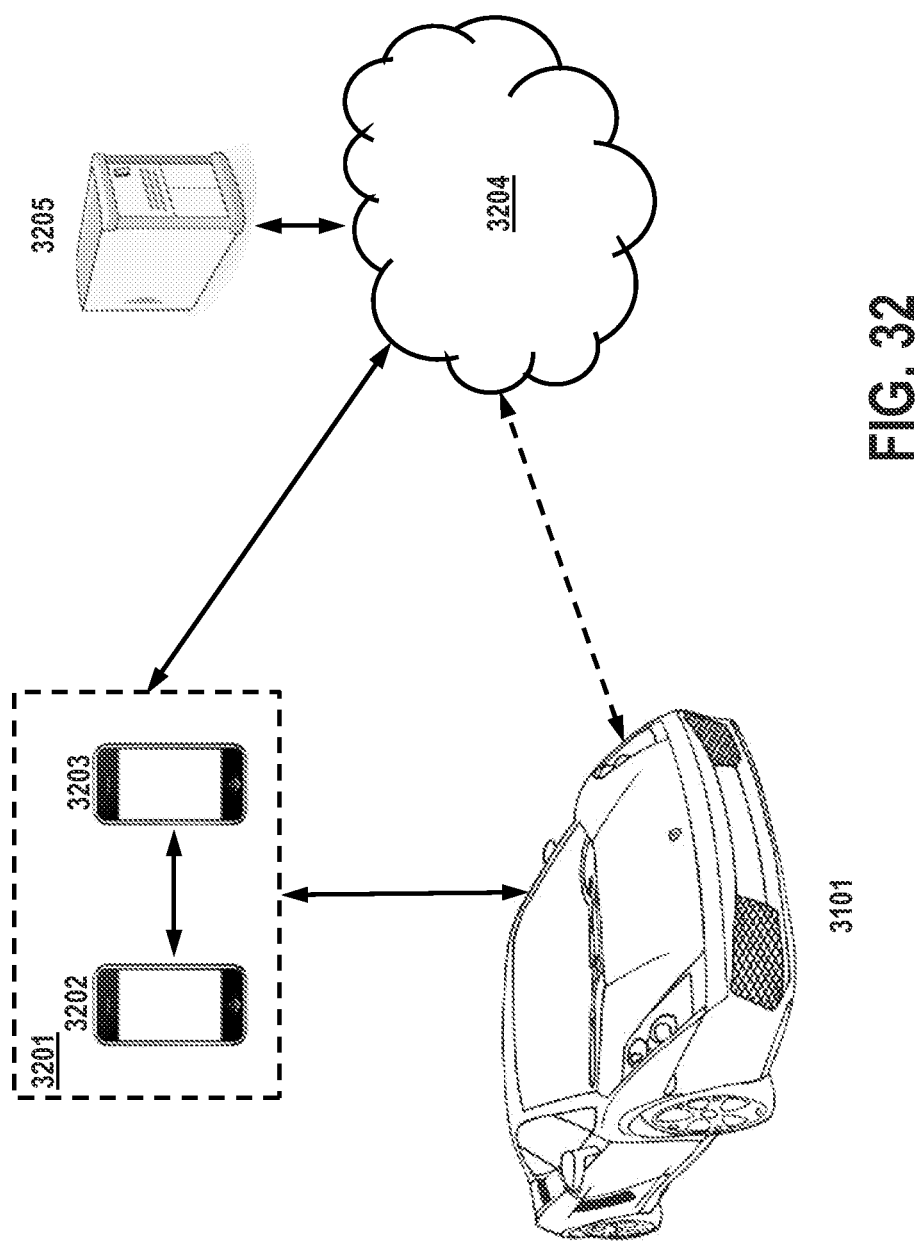

VEHICLE SEAT WITH INTEGRATED SENSORS

CROSS REFERENCE TO RELATED APPLICATIONS

This application is a U.S. national stage application of international application No. PCT/US2015/016803 filed Feb. 20, 2015, which claims priority to U.S. Provisional Application Ser. No. 61/942,543, filed Feb. 20, 2014, U.S. Provisional Application Ser. No. 61/942,513, filed Feb. 20, 2014, and U.S. Provisional Application Ser. No. 61/942,493, filed Feb. 20, 2014, The entire disclosures of PCT/US2015/016803, U.S. Ser. No. 61/942,543, 61/942,513, and 61/942,493 are hereby incorporated by reference.

BACKGROUND

The present disclosure relates to a vehicle seat, and particular to a vehicle seat including a sensor. More particularly, the present disclosure relates to a vehicle seat including one or more sensors configured to sense a physiological attribute, condition, and/or state of an occupant sitting on the vehicle seat.

SUMMARY

A vehicle seat in accordance with the present disclosure includes a seat bottom and a seat back. The seat back is coupled to the seat bottom and arranged to extend upwardly away from the seat bottom. The vehicle seat further includes an electronics system coupled to the vehicle seat.

In illustrative embodiments, the electronics system is configured to provide means for sensing a physiological attribute of an occupant sitting on the vehicle seat through impeding barriers, such as clothing worn by the occupant, so that a predetermined action may be taken in response to the physiological attribute detected by the electronics system.

In illustrative embodiments, the electronics system includes an electrocardiogram (ECG) system. The ECG system is coupled to the vehicle seat to sense electrical signals in the occupant through impeding barriers, such as the occupant's clothing, and covert the electrical signals to a heart rate of the occupant.

In illustrative embodiments, the electronics system includes an oximetry system. The oximetry system is coupled to the seat bottom to sense oxygen in the occupant's blood through impeding barriers, such as the occupant's clothing, and convert the sensed oxygen content into a respiration rate.

In illustrative embodiments, a vehicle seat sensor system for detecting and processing physiological parameters is disclosed, where the system comprises a vehicle seat, configured to accommodate an occupant, at least one oximetry sensor integrated into a first portion of the seat, wherein the oximetry sensor is configured to switch between, or select from, multiple wavelengths of light for transmission to an occupant area above a surface of the vehicle seat. The system also comprises a control system operatively coupled to the oximetry sensor, wherein the control system processes signals produced by the at least one oximetry sensor to determine a level of oxygen saturation for the occupant. The system may be configured such that the level of oxygen saturation is processed to determine at least one of a pulse transit time, blood pressure, respiration, respiration rate and respiration depth of the occupant. The vehicle sensor system may further include at least one electrocardiogram (ECG) sensor integrated into a second portion of the vehicle seat, wherein the ECG sensor is operatively coupled to the control system. The control system may be configured to processes signals produced by the ECG sensor to determine at least one of heart rate, heart rate variability, stress level, a pulse-transit time and blood pressure of the occupant.

In illustrative embodiments, a method is disclosed for detecting and processing physiological parameters from a vehicle seat sensor system, where the method includes the steps of configuring at least one oximetry sensor, integrated into a first portion of a vehicle seat to switch between, or select from, multiple wavelengths of light for transmission to an occupant area above a surface of the vehicle seat. After receiving signals from the at least one oximetry sensor, a level of oxygen saturation is detected in a control system for the occupant in the vehicle seat. The method may further include the steps of processing the detected levels of oxygen saturation in a control system to determine at least one of a pulse transit time, blood pressure, respiration, respiration rate and respiration depth of the occupant. At least one electrocardiogram (ECG) sensor may also be integrated into a second portion of the vehicle seat to receive electrical signals from the occupant, wherein the control system processes the ECG signals to determine at least one of a heart rate, heart rate variability, stress level, a pulse-transit time and blood pressure of the occupant.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which:

FIG. 1 is a perspective and diagrammatic view of a vehicle seat in accordance with the present disclosure illustrating an exemplary vehicle seat that includes a seat bottom supporting two oximetry sensors that sense an amount of oxygen in an occupant's blood through impeding barriers, such as the occupant's clothing, to provide an oximetry signal, a seat back supporting a plurality of electrocardiogram (ECG) receivers that cooperate with an ECG mat included in the seat bottom to sense electrical signals in the occupant through the occupant's clothing to provide an ECG signal, and a computer that receives the signals and processes the signals to provide a measured heart rate, blood pressure, respiration, and stress information;

FIG. 1A is an illustration of another embodiment of a vehicle seat in accordance with the present disclosure showing that a first oximetry sensor is spaced apart a first distance from a front edge of a seat bottom included in the vehicle seat and that a second oximetry is spaced apart from the front edge relatively smaller second distance so that contact by the occupant with the oximetry sensors is maximized;

FIG. 2 is a diagrammatic view of the seat back of FIG. 1 showing that the seat back includes a seat cushion and trim surrounding the seat cushion and that the ECG sensor is coupled to the seat back to lie in confronting relation with an occupant wearing multiple layers of clothing and suggesting that the ECG sensor is capable of sensing the occupant's electrical signals through the multiple layers of clothing;

FIG. 3 is a diagrammatic view of a portion of the seat bottom of FIG. 1 showing that the seat bottom includes a seat cushion and trim surrounding the seat cushion and that the oximetry sensor is coupled to the seat bottom to lie in confronting relation with the occupant wearing multiple layers of clothing and suggesting that the oximetry sensor is capable of sensing the oxygen content of the occupant's blood through the multiple layers of clothing;

Figure 1:
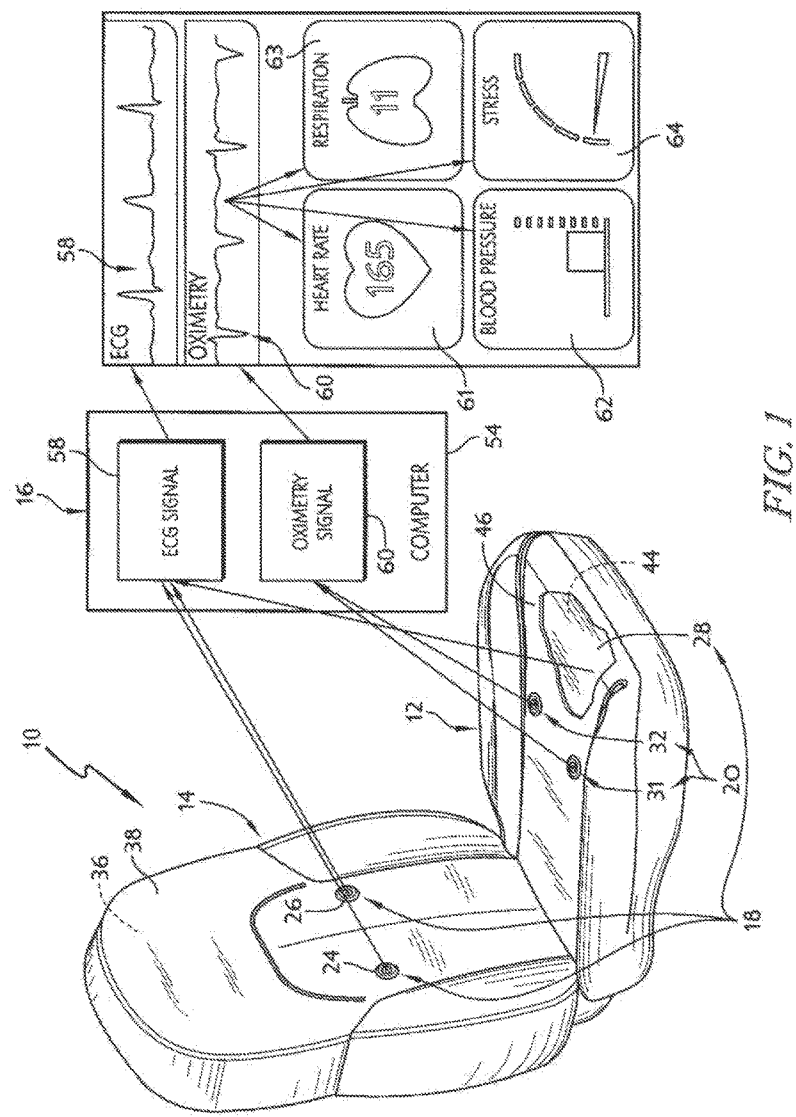
Figure 1A:
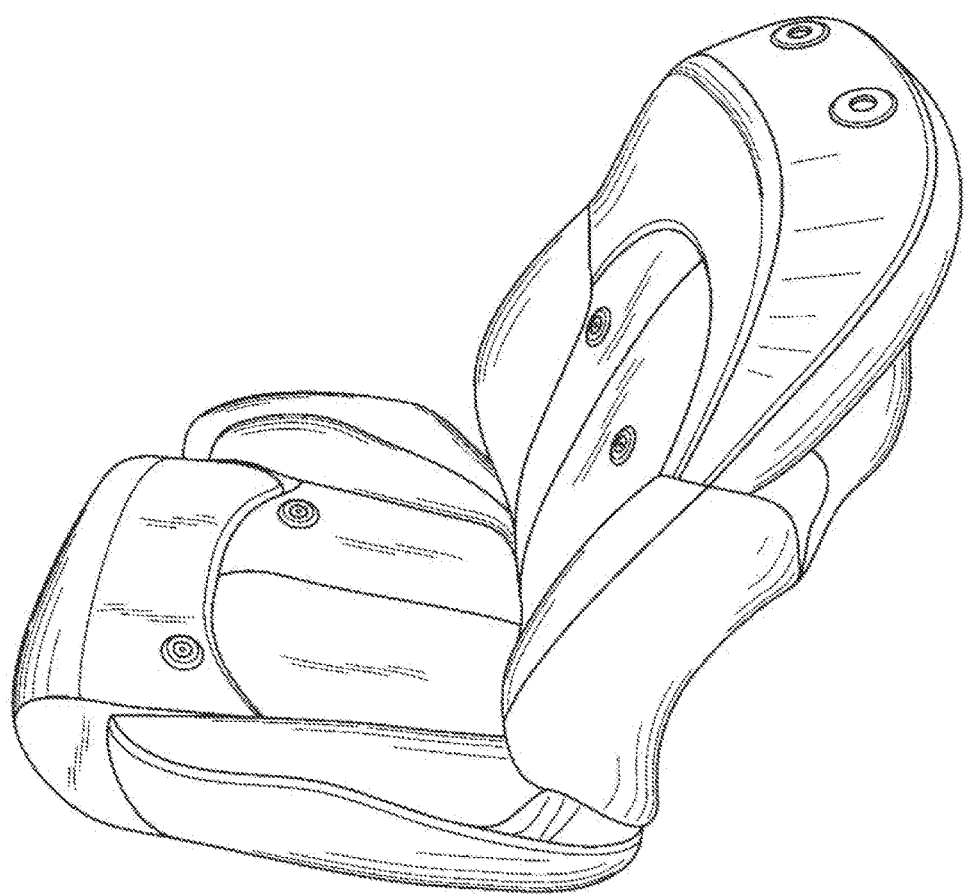
Figure 8:
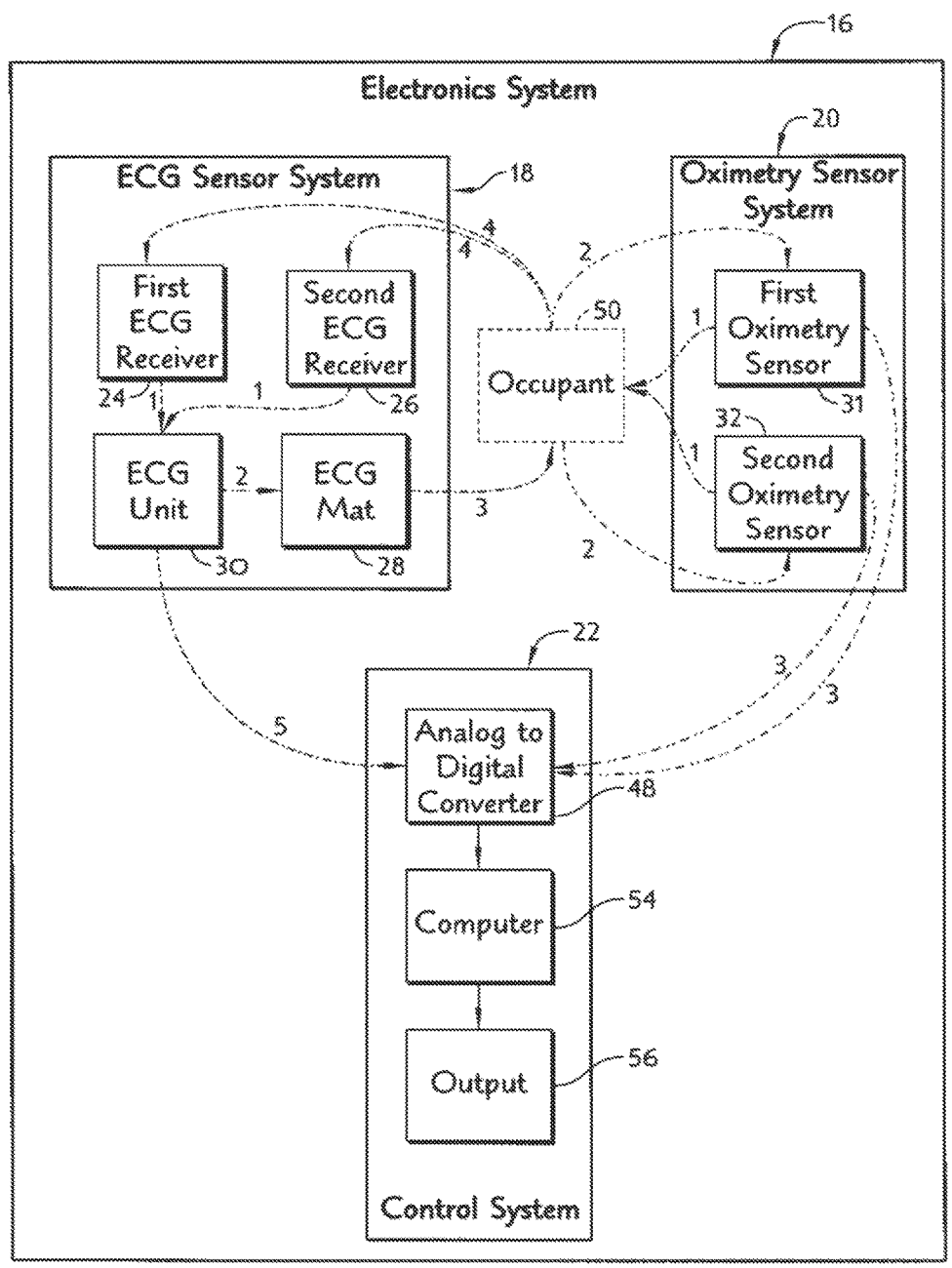
Figure 9:
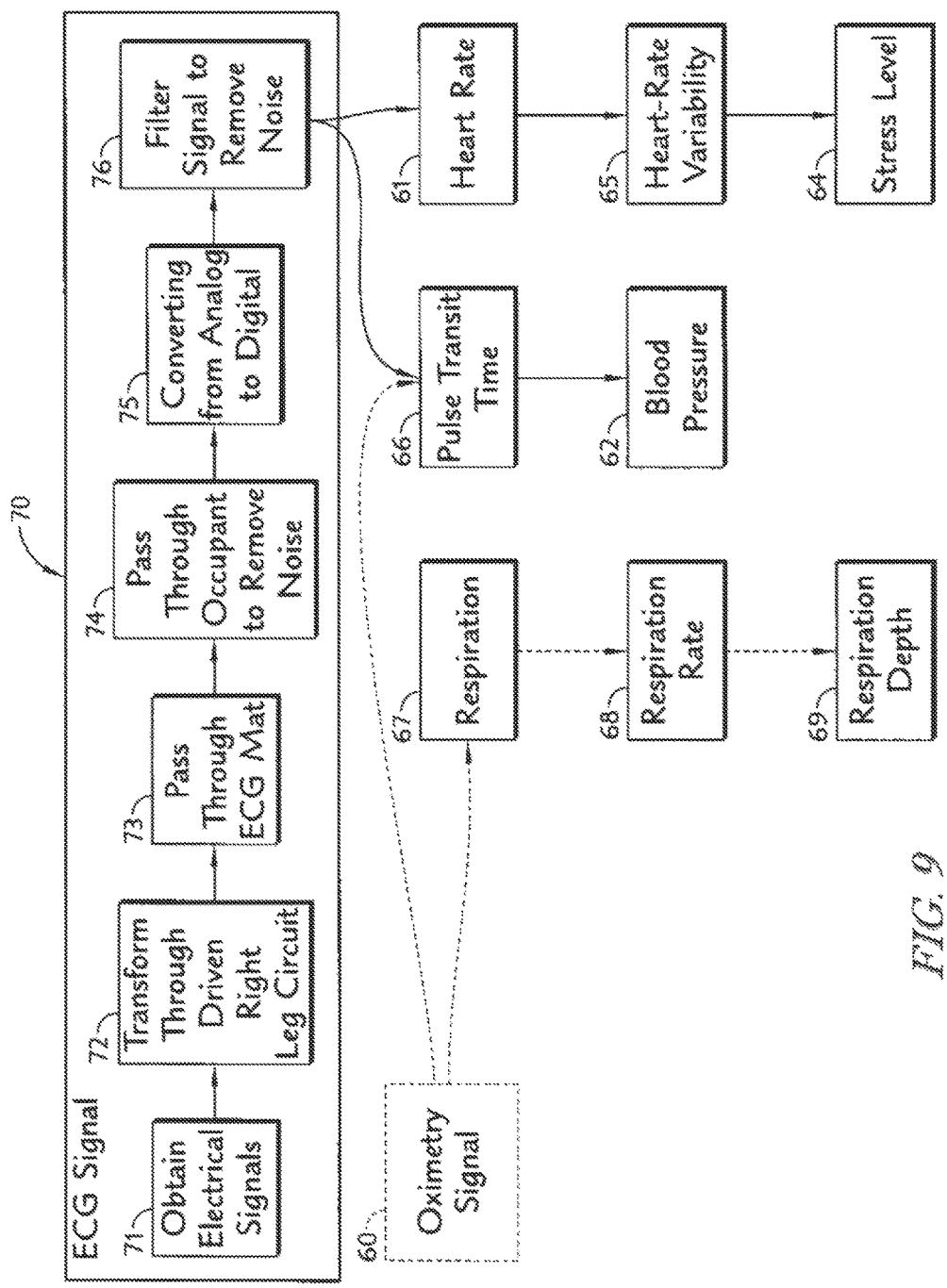
Figure 10:
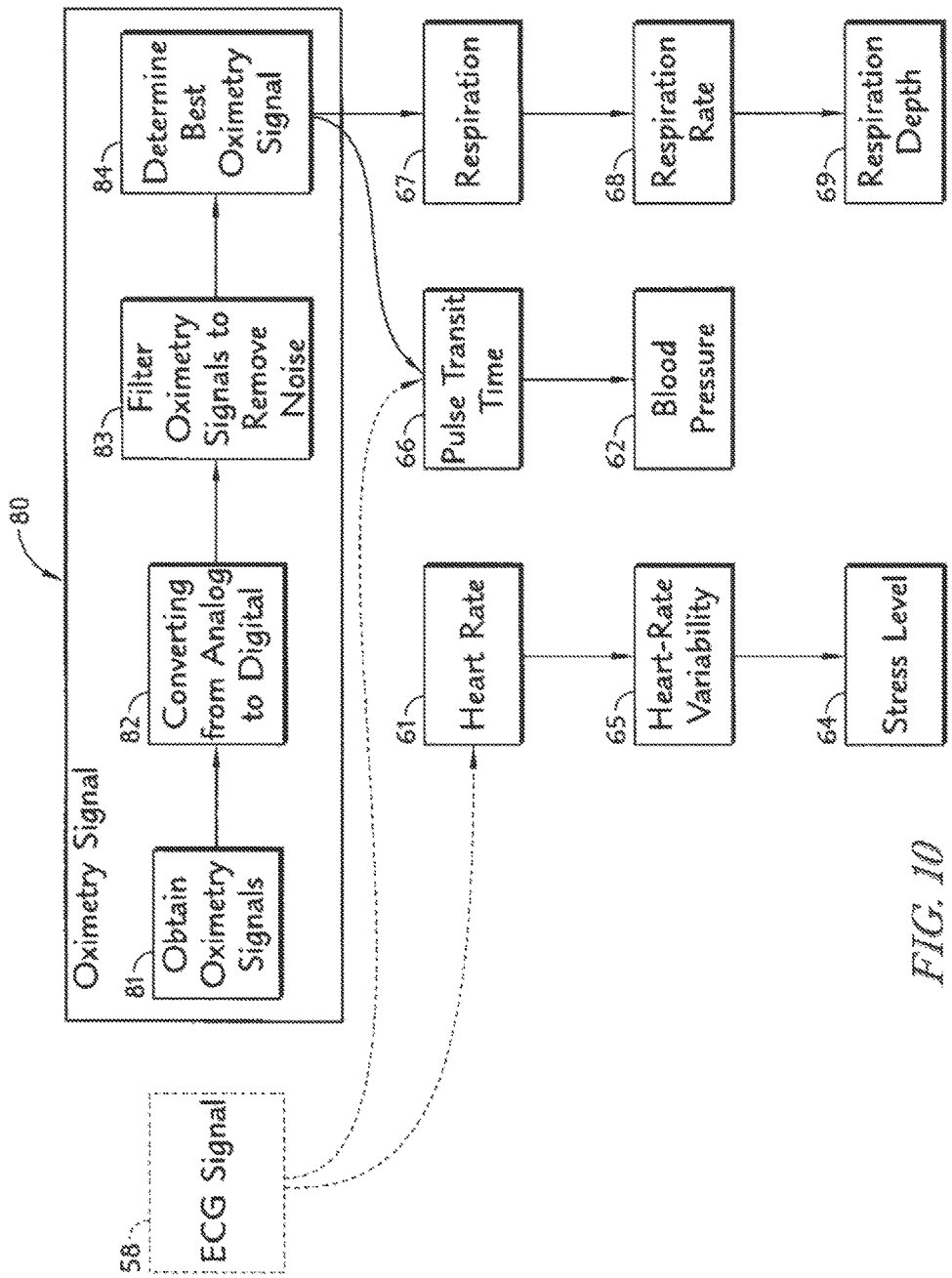
Figure 11:
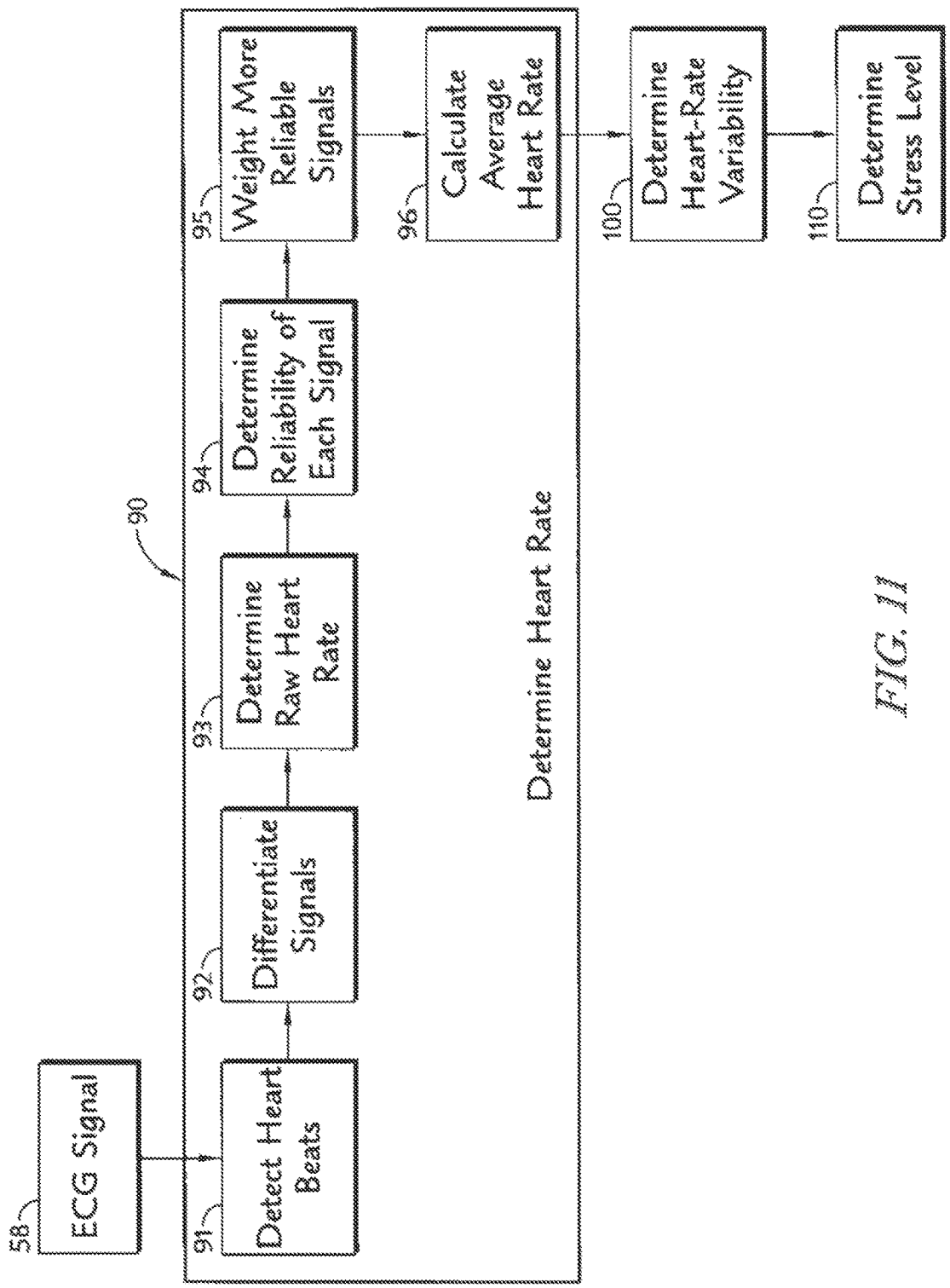
Figure 12:
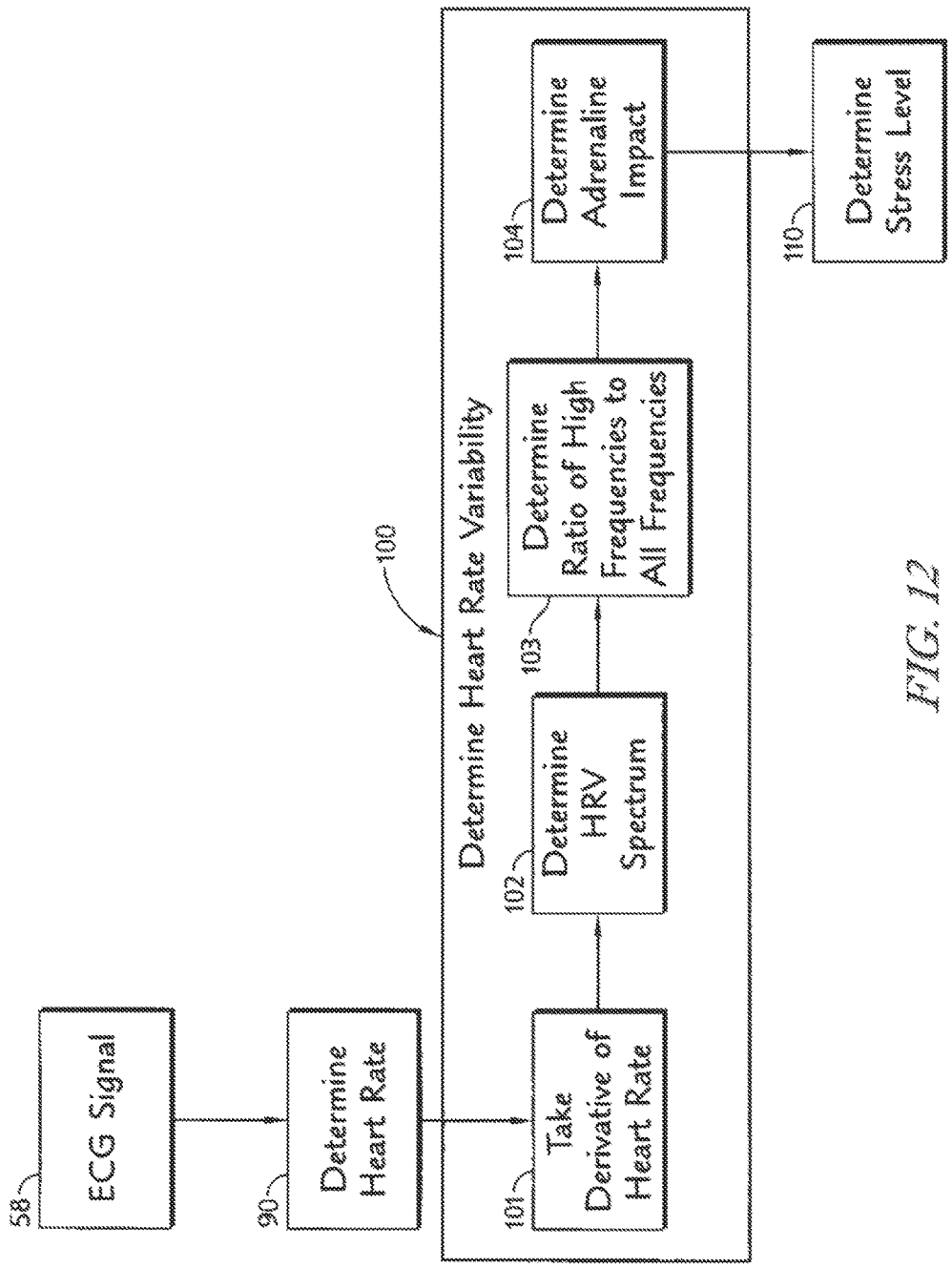
Figure 13:
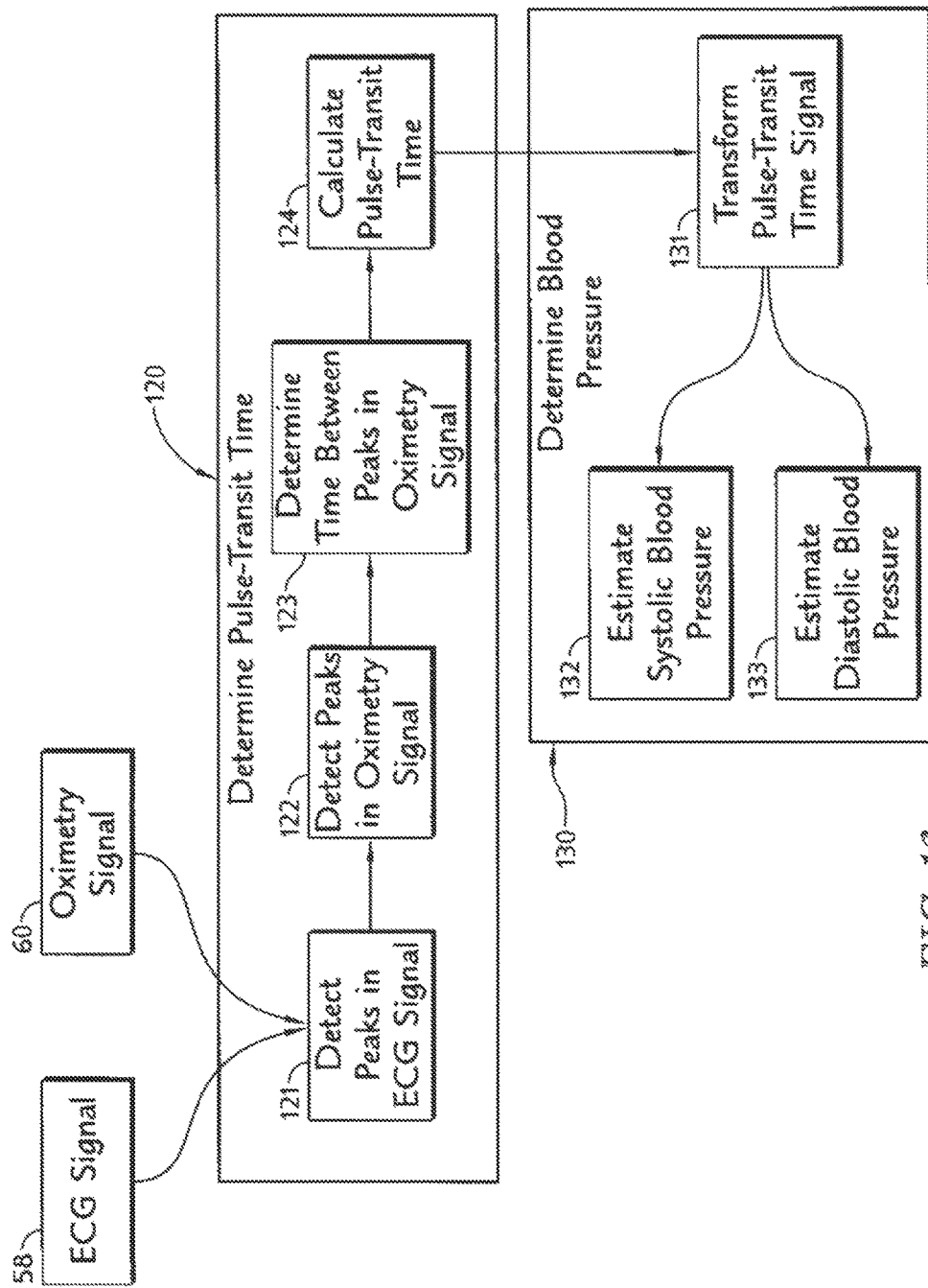
Figure 14:
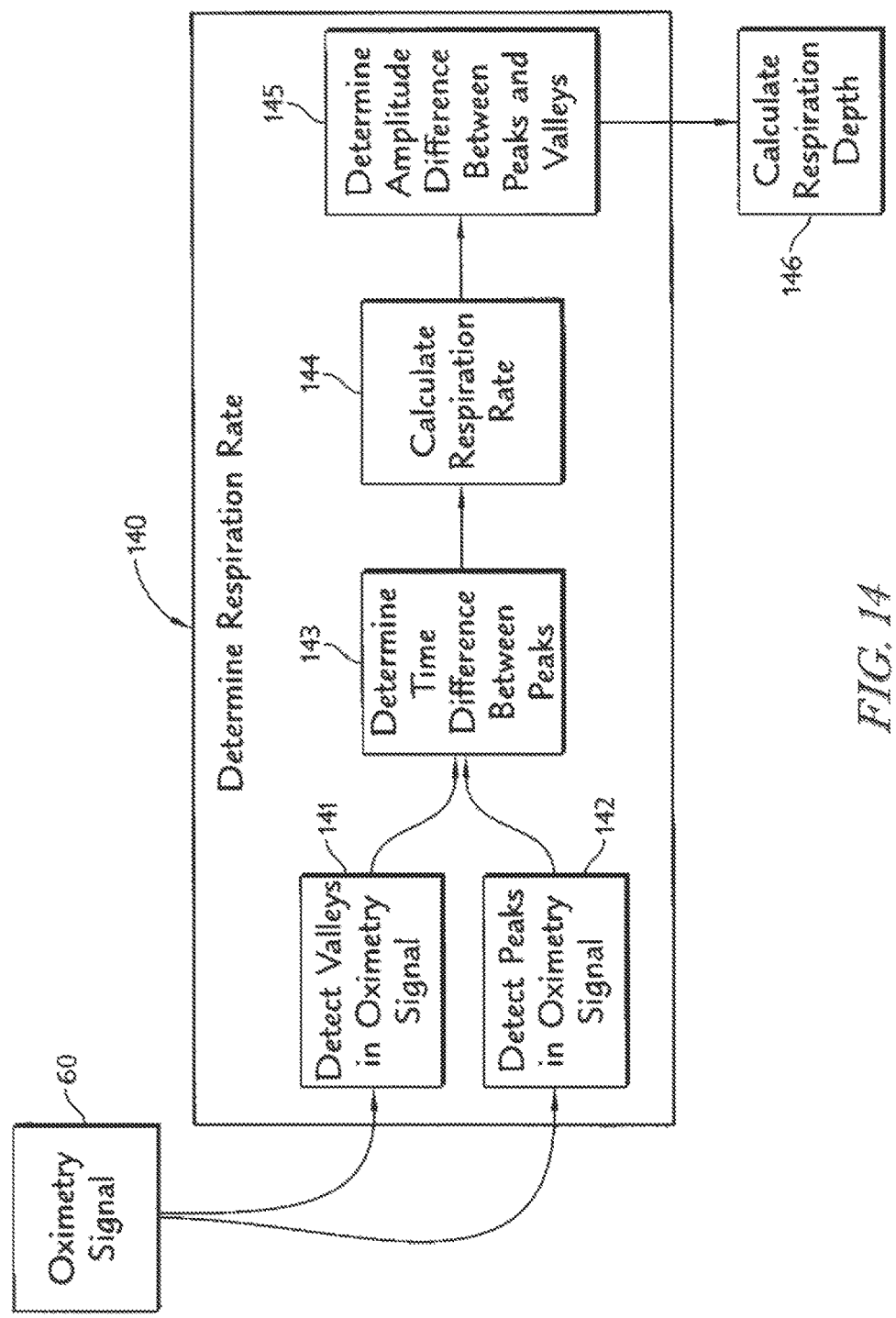
Figure 15:
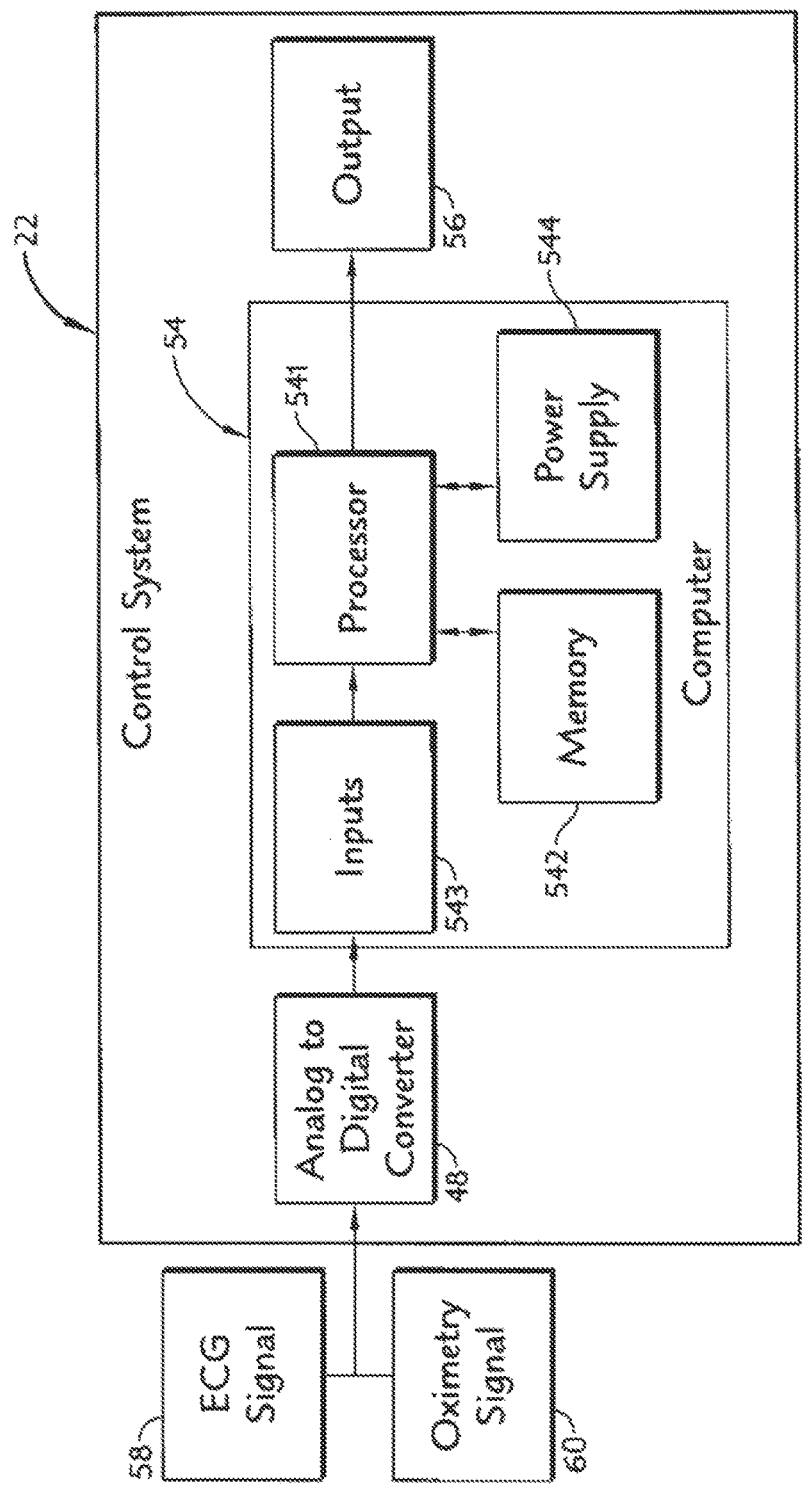
Figure 16:
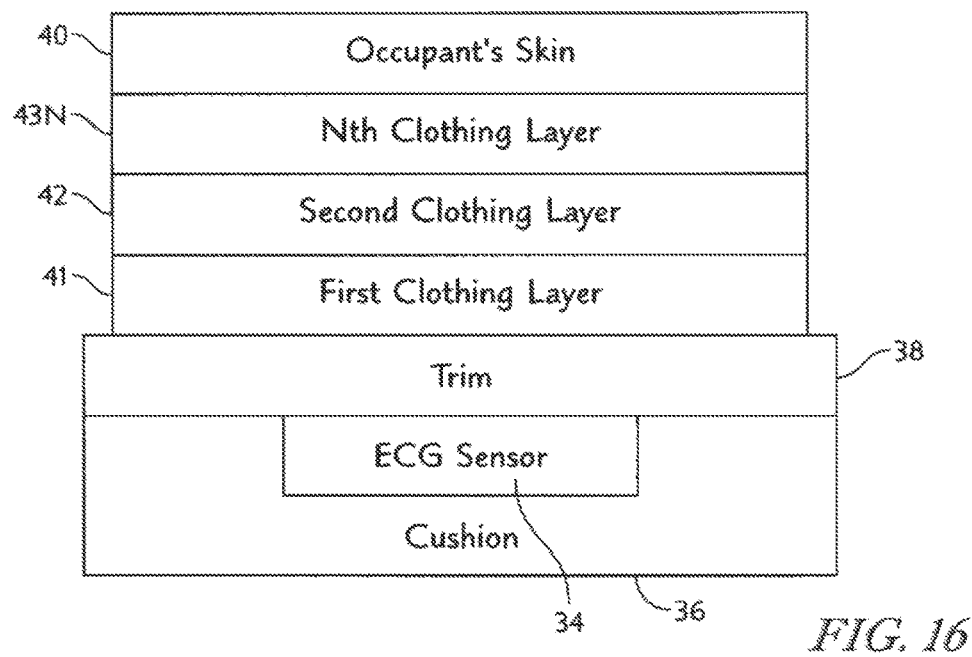
Figure 17:
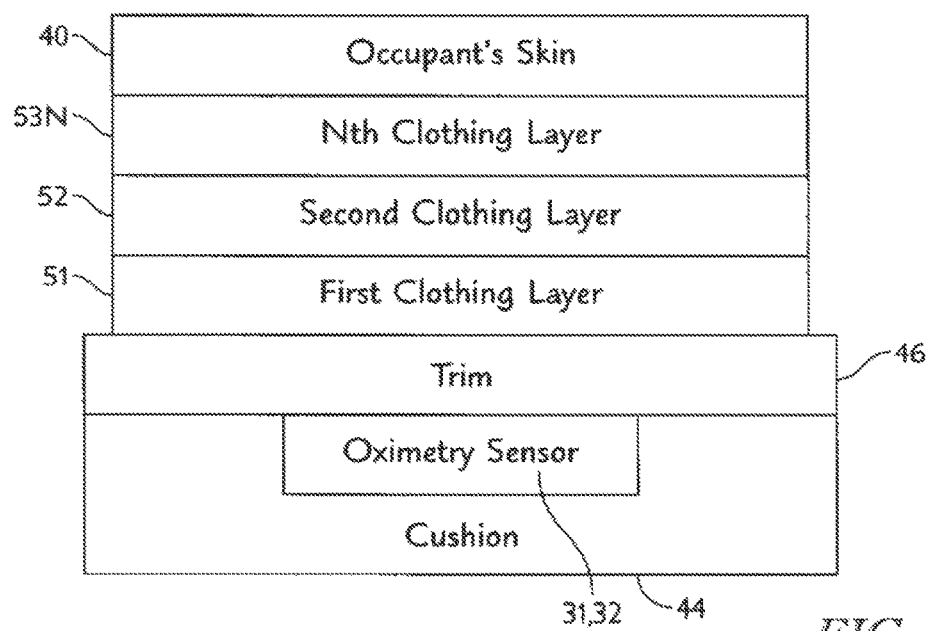
Figure 18:
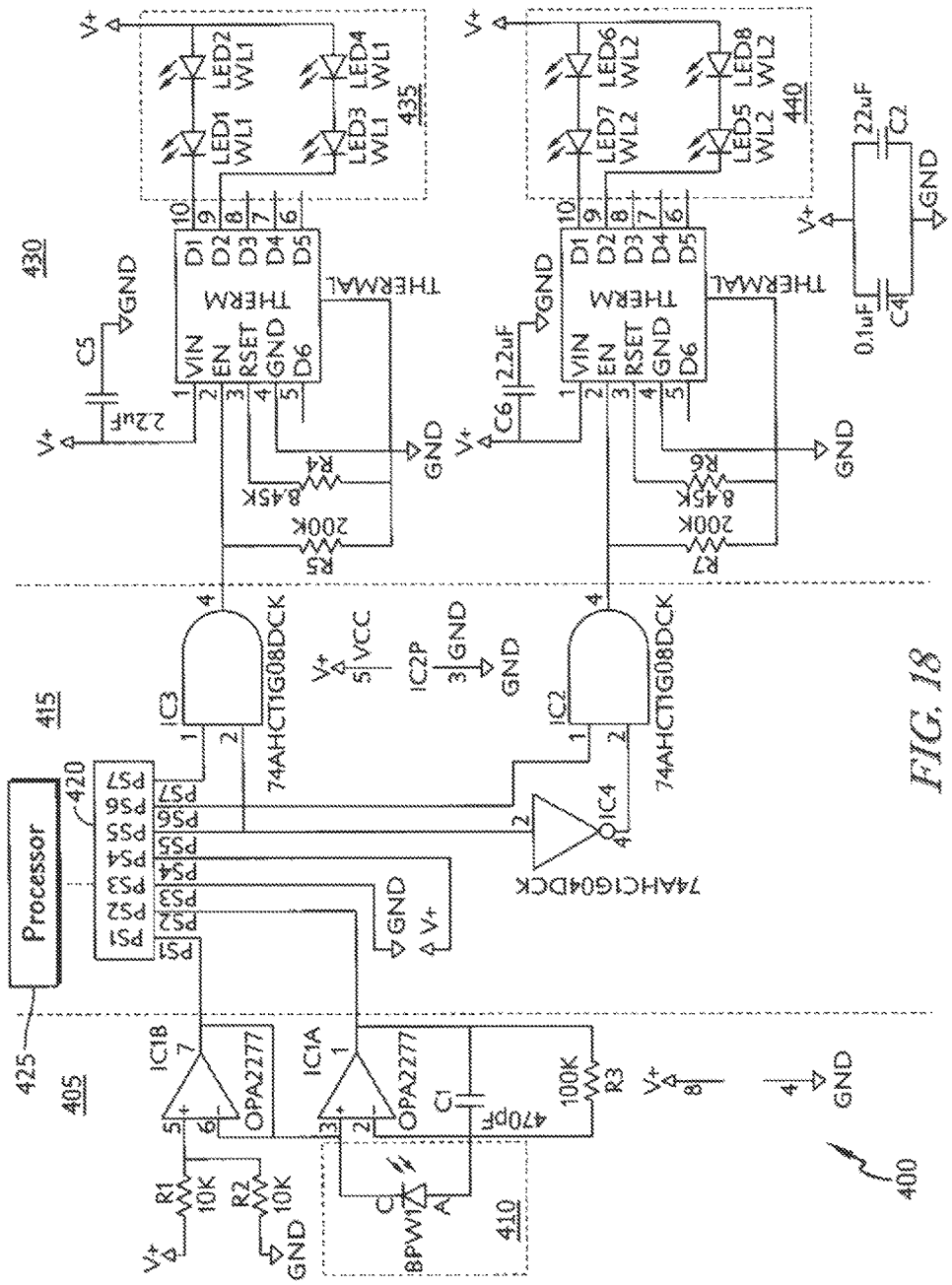
Figure 20:
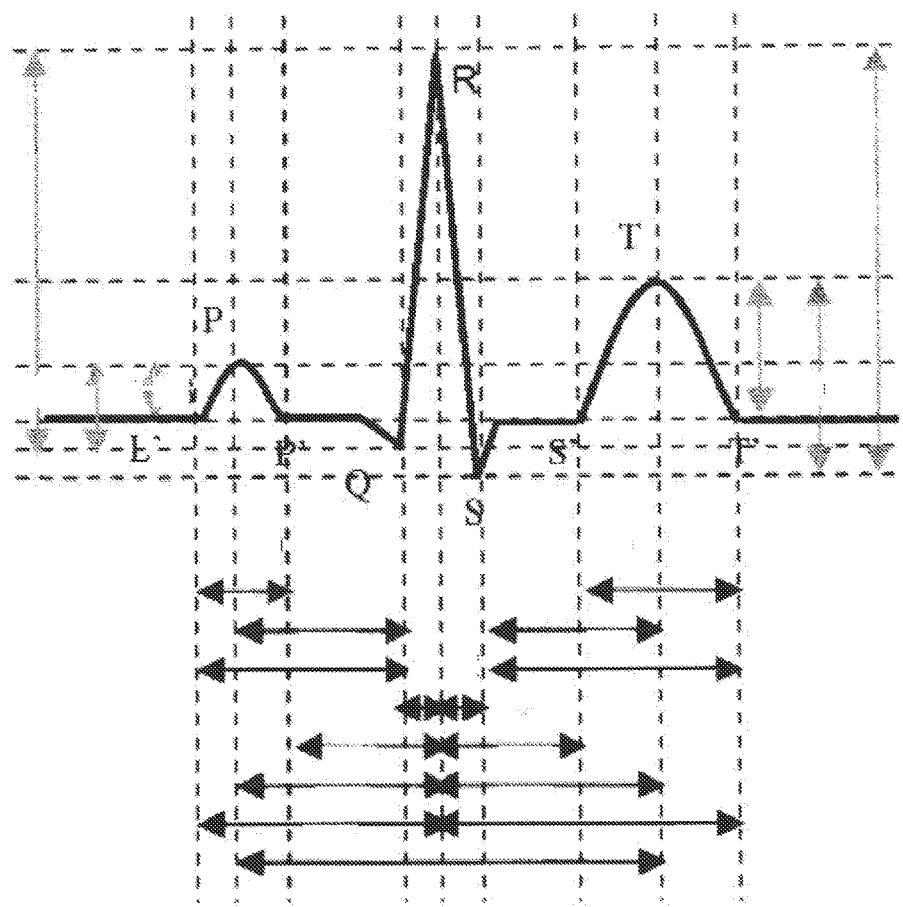
Figure 21:
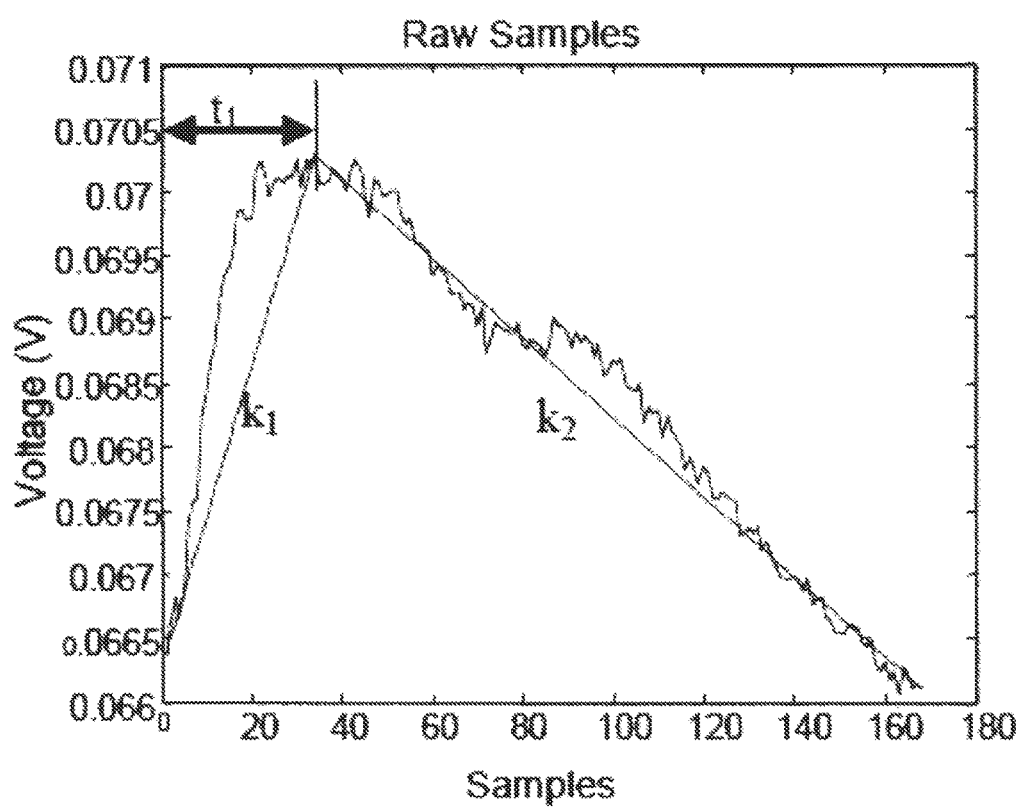
Figure 22:
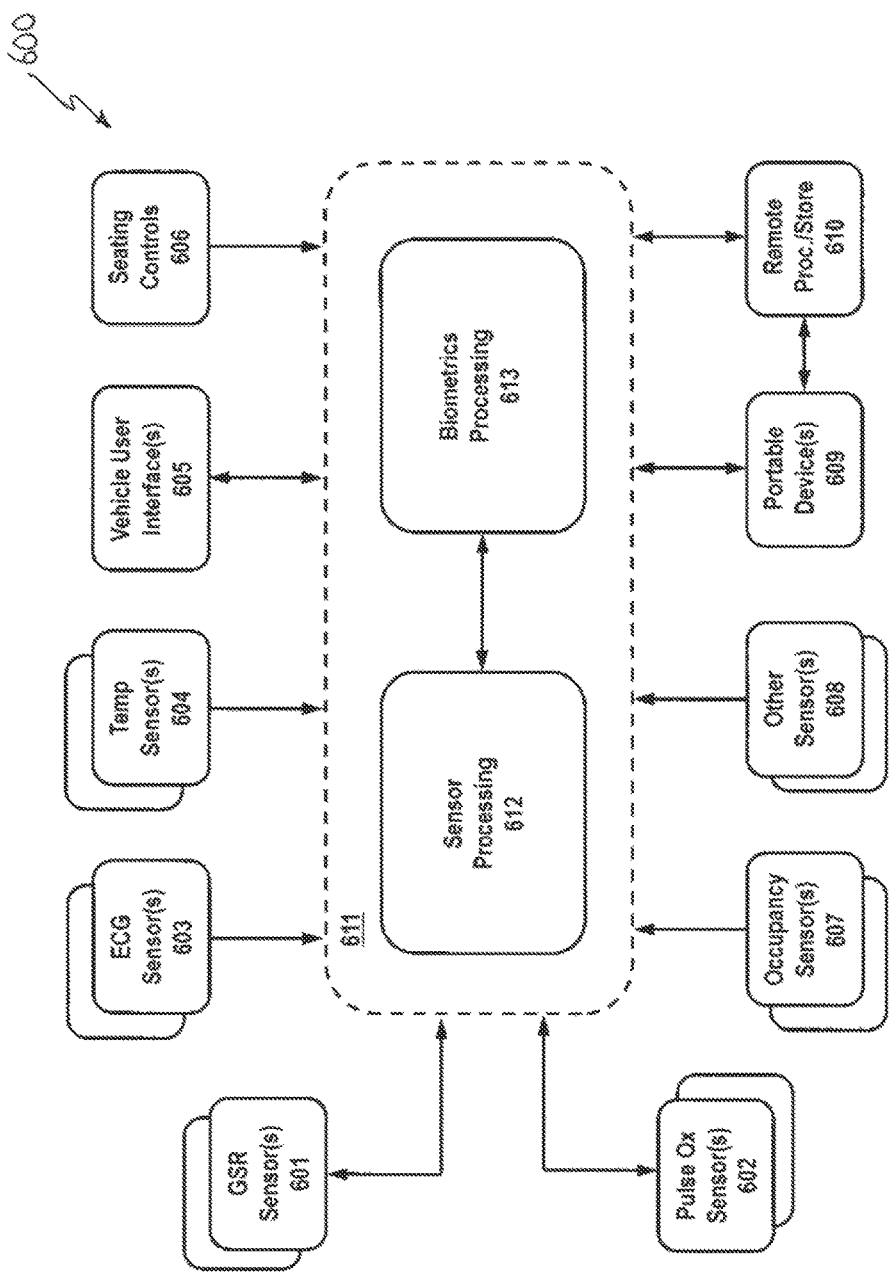
Figure 24C:
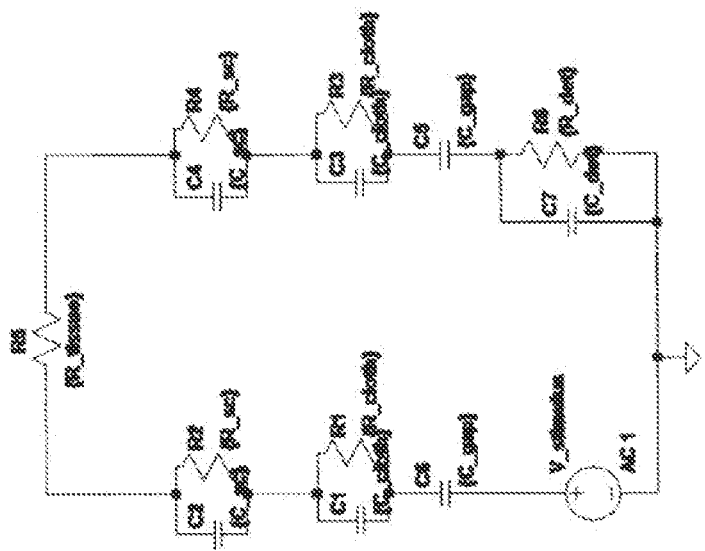
Figure 24B:
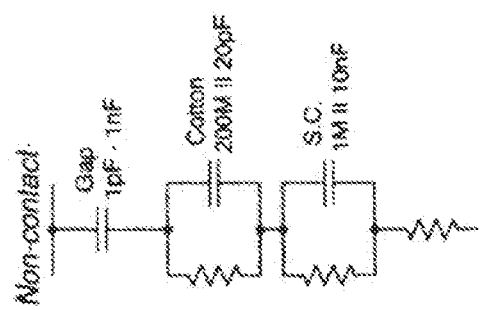
Figure 24A:
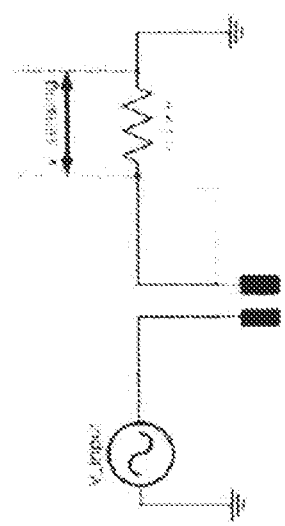
Figure 25:
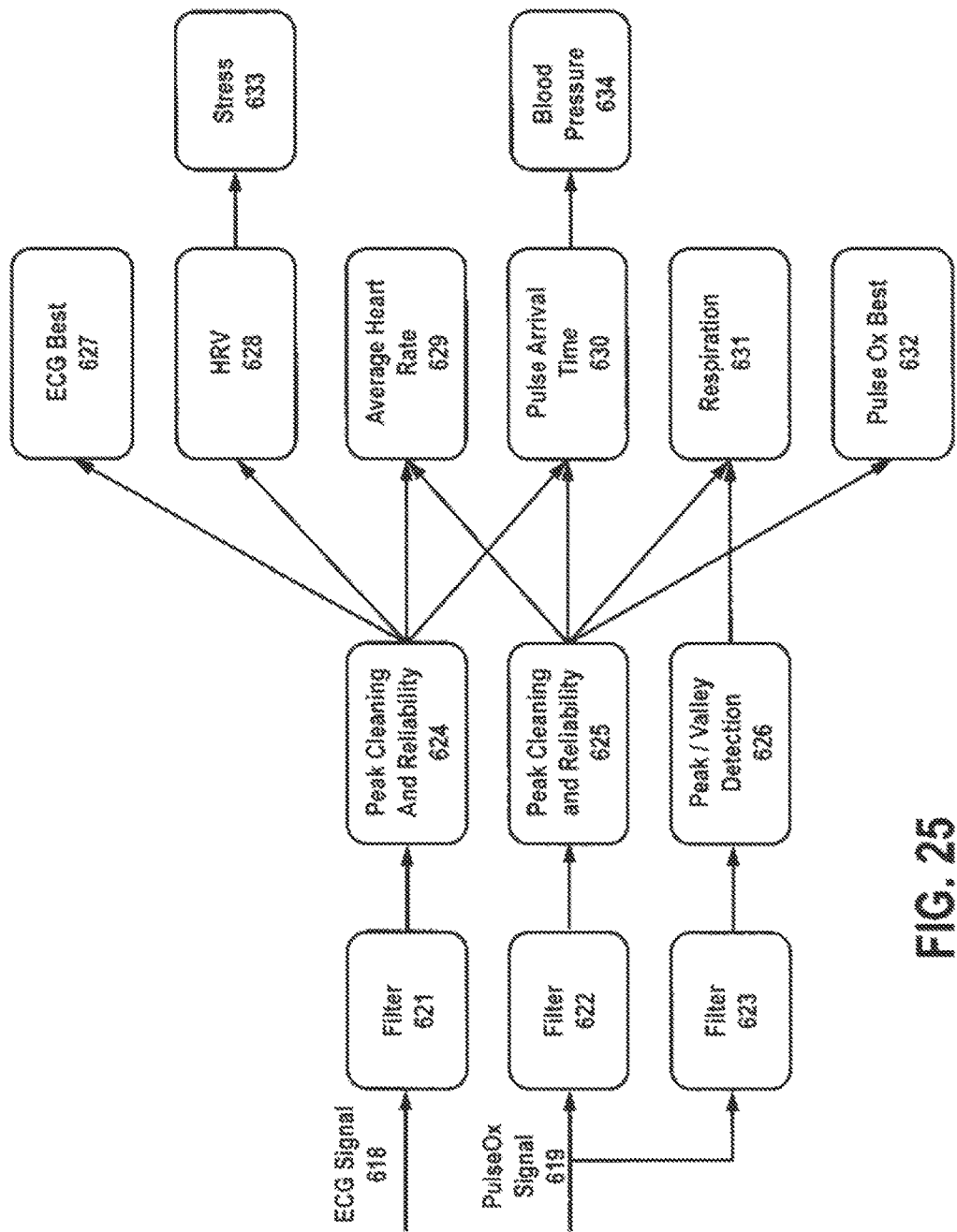
Figure 26:
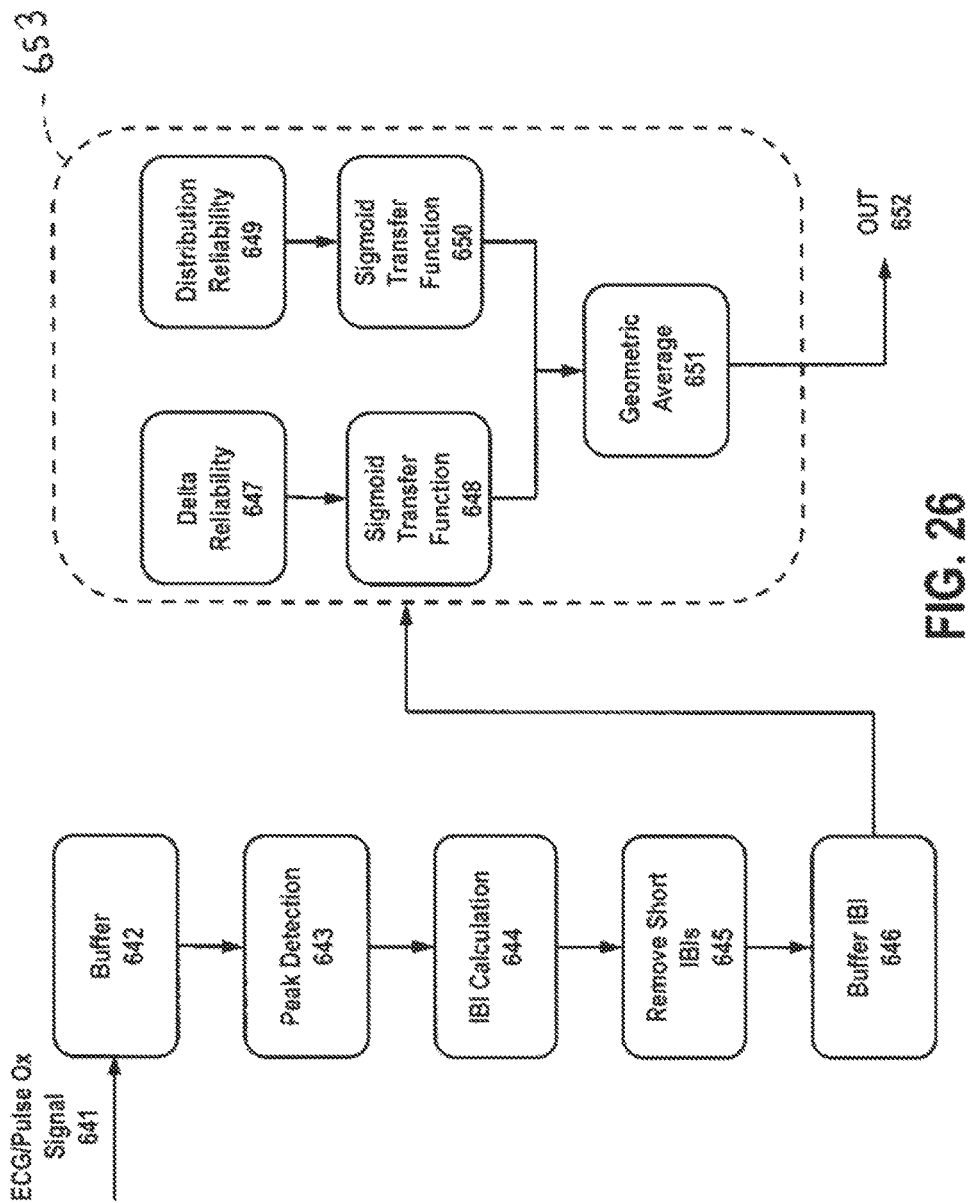
Figure 27:
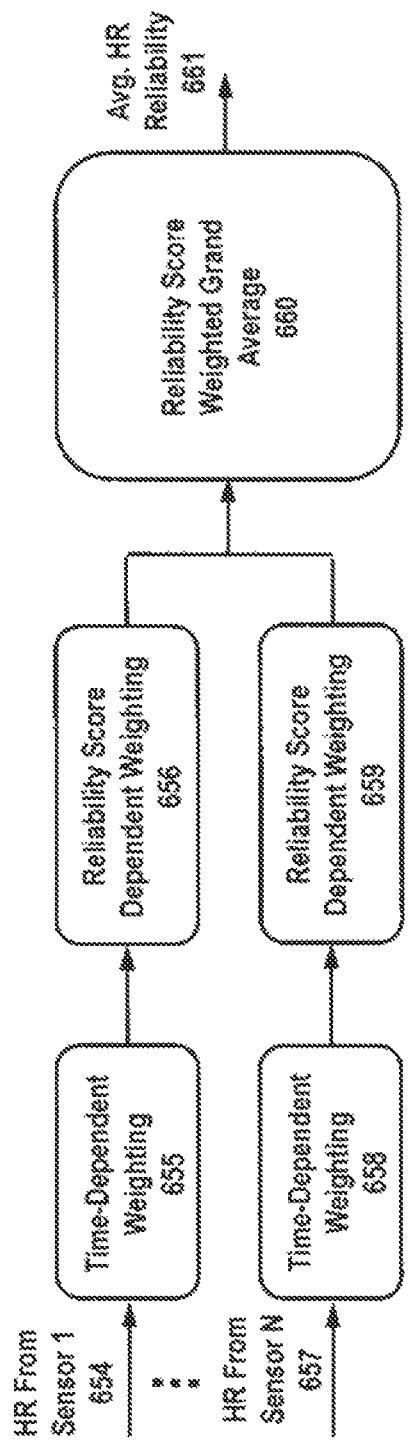
Figure 28:
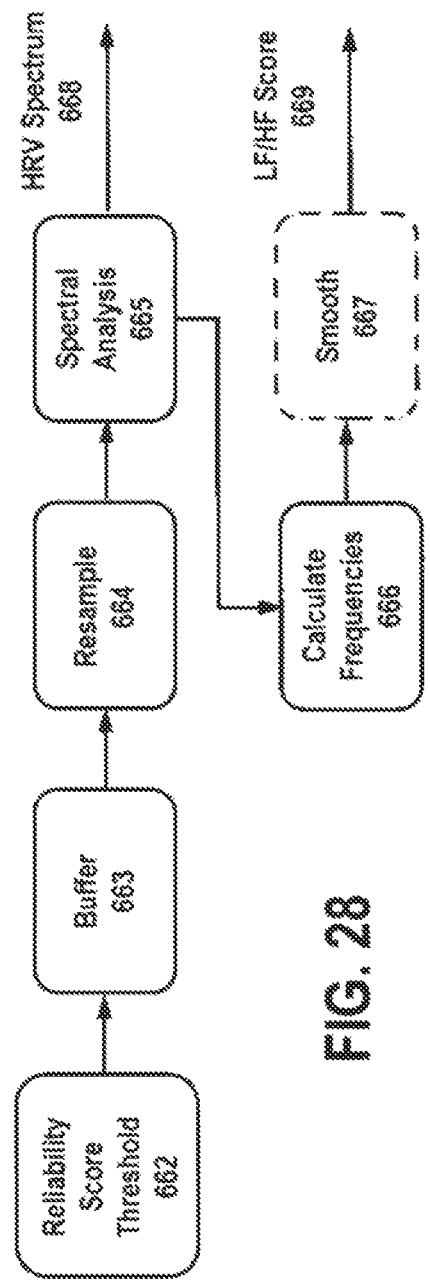
Figure 29:
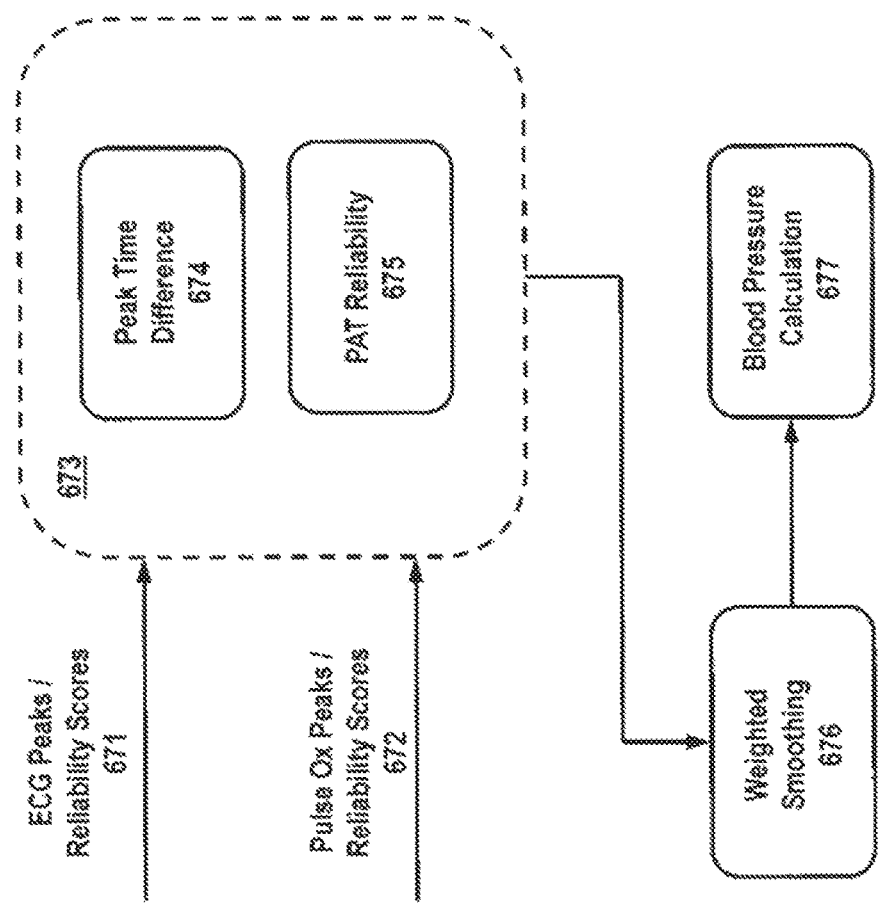
Figure 30:
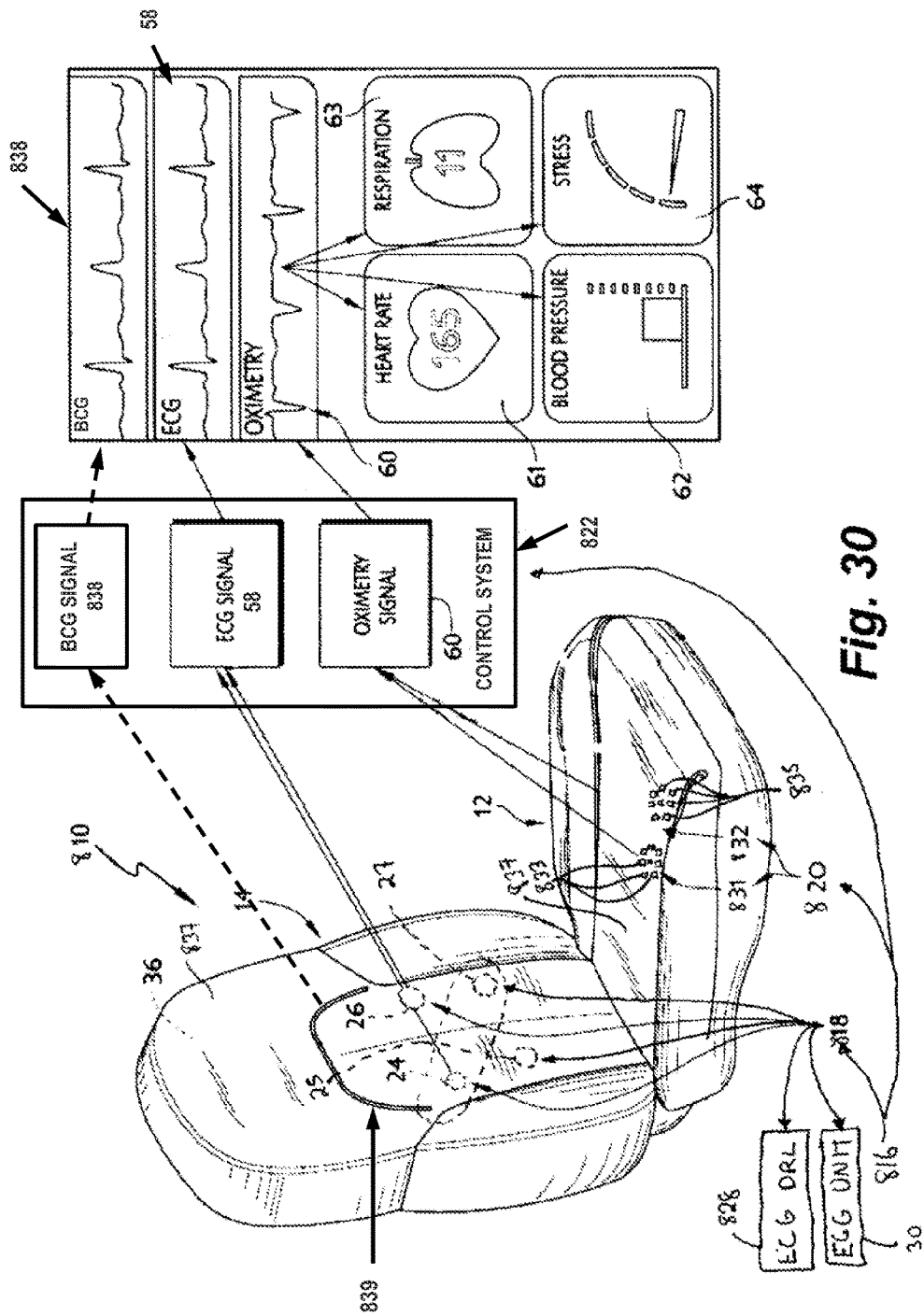
Figure 31:
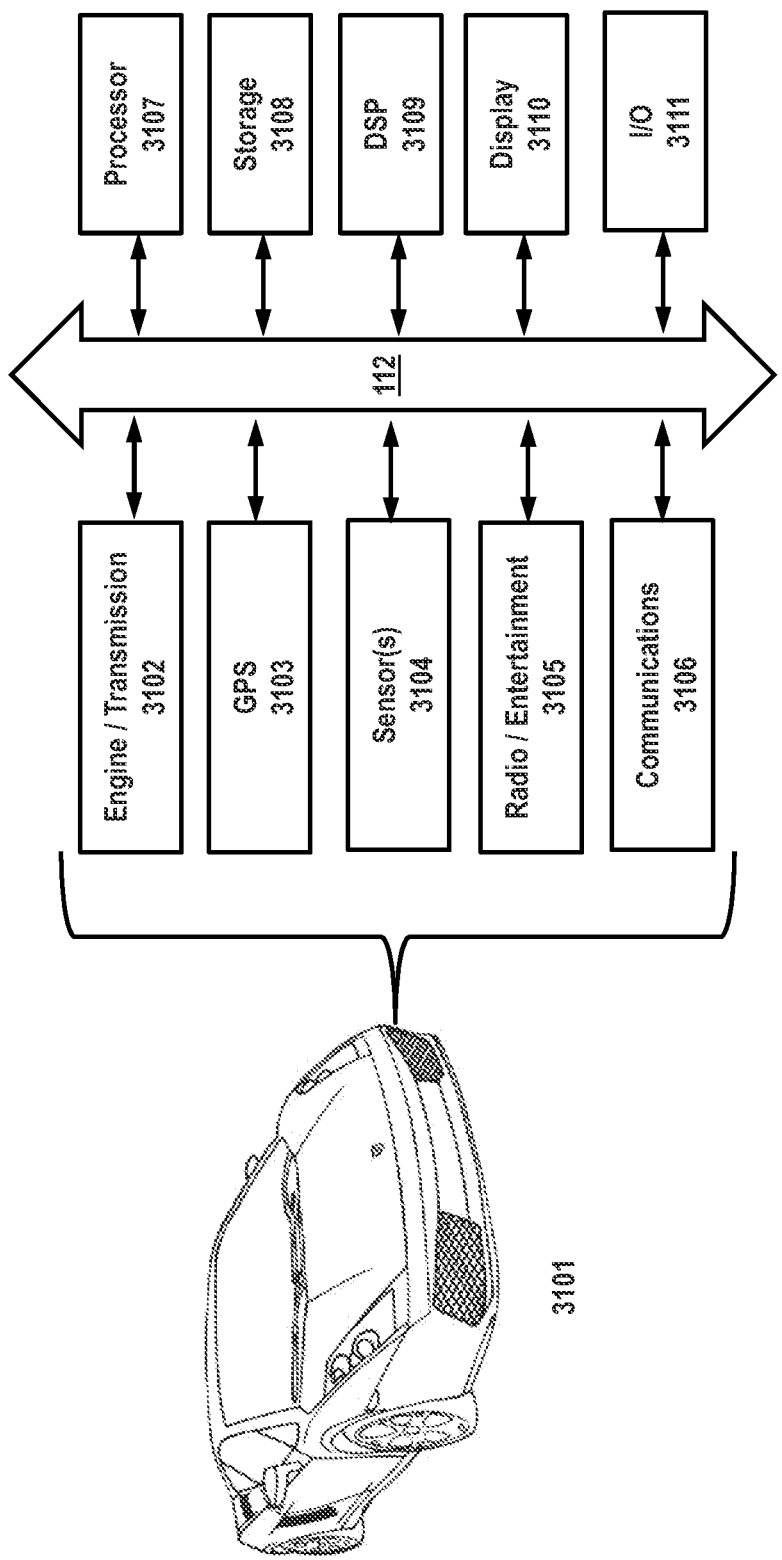

FIG. 8 is a diagrammatic view of an electronics system included in the vehicle seat of FIG. 1 showing that the electronics system includes an ECG sensor system including a first ECG receiver, a second ECG receiver, an ECG unit, and a ECG mat, an oximetry sensor system including a first oximetry sensor and a second oximetry sensor, and a control system including an analog to digital converter, a computer, and an output;

FIG. 9 is a diagrammatic view of an ECG signal-acquisition process showing that the ECG signal is acquired by obtaining electrical signals from the occupant, transforming the electrical signals through a driven right leg circuit, passing the transformed signals through the ECG-sensor mat to remove noise, passing the signals through the occupant to remove noise, converting the signal from analog to digital, and filtering the signal to remove noise and suggesting that the ECG signal may be used to determine heart rate, heart-rate variability, and stress level and combined with the oximetry signal to determine pulse-transit time and blood pressure;

FIG. 10 is a diagrammatic view of an oximetry signal-acquisition process showing that the oximetry signal is acquired by obtaining oximetry signals, converting the oximetry signals from analog to digital, filtering the signals to remove noise, and determining the best oximetry signal from the two available signals and suggesting that the oximetry signal may be used to determine respiration, respiration rate, and respiration depth and that the oximetry signal may be combined with the ECG signal to determine pulse-transit time and blood pressure;

FIG. 11 is a diagrammatic view of a heart-rate determination process including the steps of detecting heart beats from the ECG signal, differentiating the signal, determining a raw heart rate, determining reliability of each signal, weighing more reliable signals, and calculating an average heart rate;

FIG. 12 is a diagrammatic view of a heart rate variability determination process including the steps of taking the derivative of the average heart rate, determine the Heart Rate Variability (HRV) spectrum, determining a ratio of high frequencies to low frequencies, and determining the impact of adrenaline and other neurotransmitters on heart rate and suggesting that understanding which neurotransmitters are affecting heart rate may be used to determine a stress level of the occupant;

FIG. 13 is a diagrammatic view of a pulse-transit time acquisition process and a blood-pressure acquisition process showing that the pulse-transit time acquisition process includes the steps of detecting peaks in the ECG signal, detecting peaks in the oximetry signal, determining time between peaks in the oximetry signal, and calculating pulse-transit time and showing that the blood-pressure acquisition process includes the steps of transforming the pulse-transit time signal and estimating systolic blood pressure and diastolic blood pressure;

FIG. 14 is a diagrammatic view of a respiration-rate determination process including the steps of detecting peaks in the oximetry signal, detecting valleys in the oximetry signal, determining time difference between peaks, calculating a respiration rate, and determining a difference in amplitude between the peaks and valleys to calculate a respiration depth;

FIG. 15 is a diagrammatic view of the control system of FIG. 8 showing that the computer includes inputs coupled to the analog to digital converter to receive the ECG and oximetry signals, a processor configured to execute instructions stored in memory, and a power supply coupled to the processor to provide power;

FIG. 16 is a diagrammatic view of another embodiment of a seat back in accordance with the present disclosure showing that the seat back includes a seat cushion and trim surrounding the seat cushion and that an ECG sensor may be coupled to the seat cushion to lie below the trim to sense an occupant's electrical signals through the trim and multiple layers of clothing;

FIG. 17 is a diagrammatic view of another embodiment of a seat bottom in accordance with the present disclosure showing that the seat bottom includes a seat cushion and trim surrounding the seat cushion and that the oximetry sensor may be coupled to the seat cushion to lie below the trim to sense oxygen content of the occupant's blood through impeding barriers, such as the trim and multiple layers of clothing;

FIG. 18. is an exemplary schematic diagram showing electronic components included in an oximetry sensor assembly provided in accordance with the present disclosure;

FIG. 19 provides a table that includes additional information regarding the electronic components shown in FIG. 18;

FIG. 20 is a graph showing an illustrative ECG signal and associated data points taken from the ECG signal used establish an identity of an occupant to which the ECG signal is obtained therefrom;

FIG. 21 is a graph showing an illustrative photoplethysmographic (PPG) pulse and associated data points taken from the PPG pulse used to establish identity of an occupant to which the PPG pulse is obtained therefrom;

FIG. 22 is a diagrammatic view of another embodiment of a seat sensor system in accordance with the present disclosure;

FIG. 23 is a diagrammatic view of an illustrative non-contact GSR sensor used to detect a galvanic skin response of an occupant;

FIG. 24A is a diagrammatic view of an experimental setup of a non-contact GSR sensor with an AC signal delivered to one electrode included in the non-contact GSR sensor placed under a thigh of an occupant and a read electrode included in the non-contact GSR measuring the skin resistance of the occupant;

FIG. 24B is a diagrammatic view of an electrical model of the experimental setup of FIG. 24A showing the resistive and capacitive properties of various features of the setup such as a gap between the sensor, the occupant's clothing, and the occupant's skin;

FIG. 24C is a diagrammatic view of a full electrical model of the experimental setup of FIG. 24A and FIG. 24B;

FIG. 25 is a diagrammatic view showing how sensor signals are processed to provide biological data associated with an occupant and resultant outputs calculated from the biological data;

FIG. 26 is a diagrammatic view showing how sensor signals may be evaluated by using peak detection and calculating reliability scores to maximize performance of the electronics system to provide biological data;

FIG. 27 is a diagrammatic view showing how an average heart rate may be calculated using heart rate signals from various heart rate sensors and reliability of each sensor;

FIG. 28 is a diagrammatic view showing how heart rate variability may be determined biological data taken from either the pulse ox signal or the ECG signal;

FIG. 29 is a diagrammatic view showing how blood pressure is calculated using pulse transit time calculated from biological data determined from both the pulse ox signals and the ECG signals;

FIG. 30 is a perspective and diagrammatic view of another embodiment of a vehicle seat in accordance with the present disclosure showing that the vehicle seat includes a seat bottom supporting two oximetry sensors that sense an amount of oxygen in an occupant's blood through impeding barriers, such as the occupant's clothing, to provide an oximetry signal, a seat back supporting a four electrocardiogram (ECG) receivers that cooperate with an ECG Driven Right Leg (DRL) unit included in the vehicle to sense electrical signals in the occupant through the occupant's clothing to provide an ECG signal, and a control system that receives the signals and processes the signals to provide a measured heart rate, blood pressure, respiration, stress information, and other biological data;

FIG. 31 is an illustrative embodiment of a vehicle system block diagram in accordance with the present disclosure, comprising a plurality of modules coupled to a vehicle bus that include an engine/transmission module, vehicle and seat sensor modules, communications module, a processor, storage, digital signal processing, a display and an input-output module for interacting vehicle components with the seat sensor signals; and FIG. 32 is an illustrative embodiment of a vehicle communications system in accordance with the present disclosure, wherein a vehicle may communicate with one or more external devices, and each may be configured to communicate to at least one server over a network.

DETAILED DESCRIPTION

A vehicle seat 10, in accordance with the present disclosure, includes a seat bottom 12, a seat back 14, and an electronics system 16 as shown FIG. 1 and suggested in FIG. 8. Seat back 14 is coupled to seat bottom 12 to extend in an upward direction away from seat bottom 12. Electronics system 16 is configured to sense one or more physiological attributes of an occupant (not shown) sitting on vehicle seat 10 through impeding barriers, such as clothing worn by the occupant, so that a predetermined action may be taken in response to the physiological attribute detected by electronics system 16. In some illustrative examples, the predetermined action may include, but is not limited to, generating a control signal, generating audio and/or visual indicia, performing a mechanical and/or electromechanical adjustment to a device, apparatus or module in a vehicle, or providing tactile feedback by vehicle seat 10, or other suitable device, to the occupant.

As shown in FIG. 8, electronics system 16 comprises an electrocardiogram (ECG) sensor system 18, an oximetry sensor system 20, and a control system 22. ECG sensor system 18 is coupled to seat back 14 and seat bottom 12 to sense electrical signals provided by the occupant. Oximetry sensor system 20 is coupled to seat bottom 12 to sense oxygen content in the occupant's blood. Control system 22 is coupled to the ECG sensor system 18 and oximetry sensor system 20 to receive signals provided by each system, process the signals, make calculations using the signals, and determine physiological attributes of the occupant. Control system 22 may perform one or more predetermined actions based on the physiological attributes of the occupant.

ECG sensor system 18 of FIG. 8 includes, for example, a first ECG receiver 24, a second ECG receiver 26, an ECG mat 28, and an ECG unit 30 as suggested in FIGS. 1, 2, 4, 5, and 8. First and second ECG receivers 24, 26 are coupled to seat back 14 to lie in spaced-apart relation to one another and lie in spaced-apart relation above seat bottom 12. ECG mat 28 is coupled to seat bottom 12 and arranged to lie under the thighs of an occupant 50. In one example, ECG receivers 24, 26 are aligned with an occupant's chest and arranged to sense electrical signals provided by the occupant's body. The sensed electrical signals are then transformed by a driven right leg circuit included in ECG unit 30, and passed through ECG mat 28 located in seat bottom 12 as suggested in FIG. 8. ECG mat 28 then sends the signals back through occupant 50 where the signals are detected again by ECG receivers 24, 26, passed through ECG unit 30 and sent to control system 22. As a result, ECG sensor system 18 minimizes noise so that the remaining signal is associated more closely with an occupant's heart rate.

Figure 2:
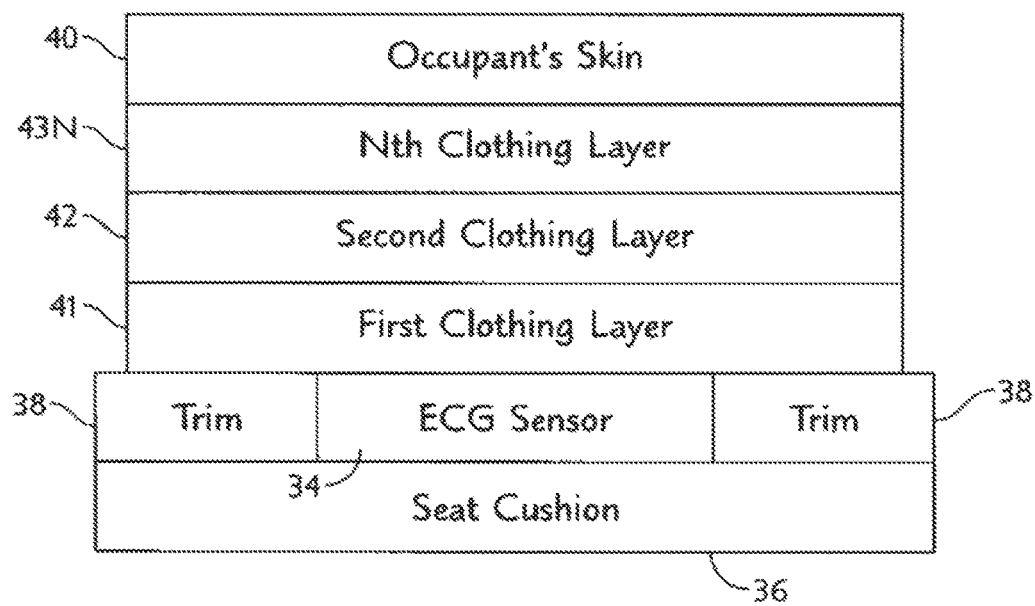

First and second ECG receivers 24, 26 and ECG mat 28 cooperate to provide an ECG sensor 34. ECG sensor 34 is coupled to a seat cushion 36 and surrounded by trim 38 as shown in FIG. 2. ECG sensor 34 is configured to provide means for detecting electrical signals in occupant 50 through first, second, and $N^{th}$ clothing layers 41, 42, and 43N as shown in FIG. 2. In one example, first clothing layer 41 is a shirt made of cotton. Second clothing layer 42 is an undershirt made from cotton. Nth clothing layer 43N may be yet another undershirt made from polyester. $N^{th}$ clothing layer 43N may be one layer or may be additional layers.

Figure 3:
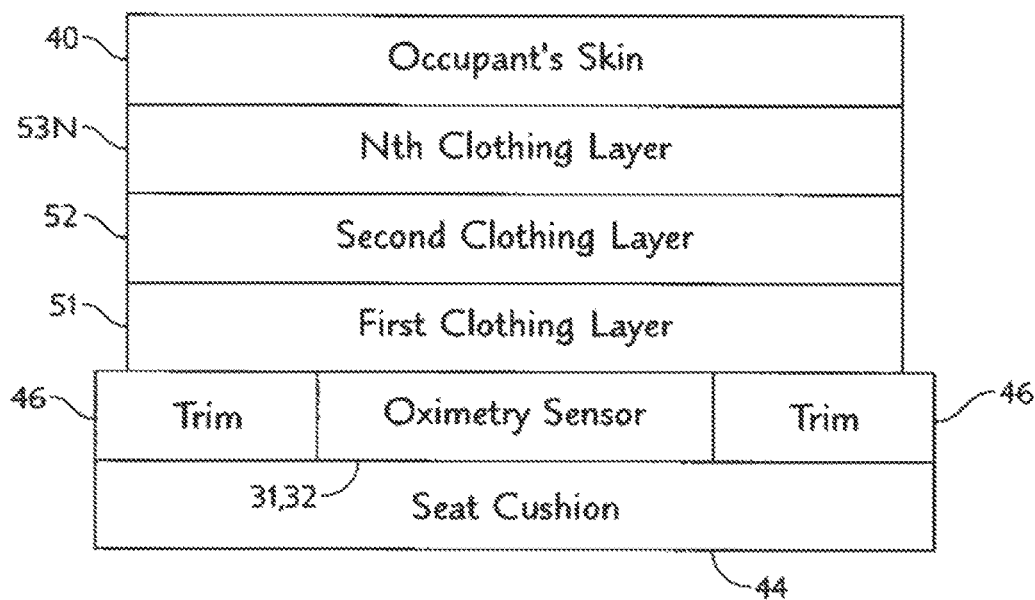
Figure 4:
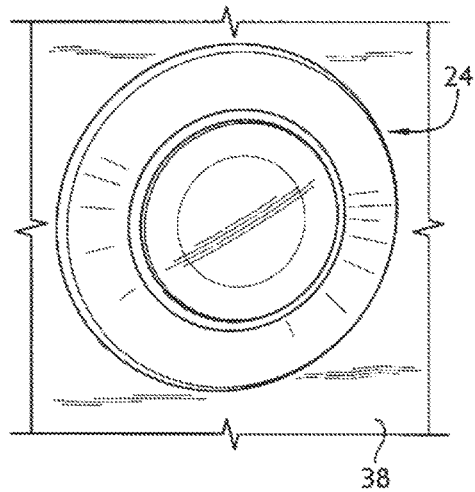
FIG. 4 is an enlarged partial perspective view of the ECG sensor of FIG. 1.
Figure 5:
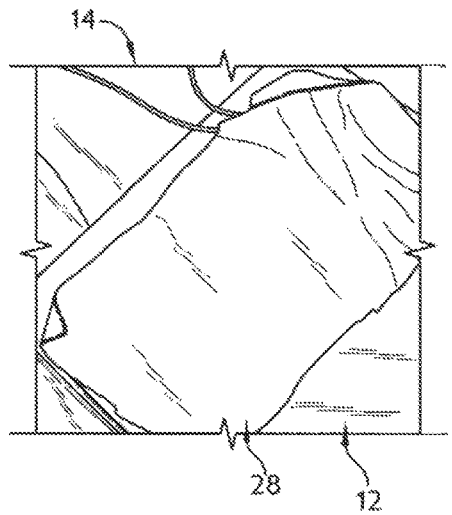
FIG. 5 is an enlarged partial perspective view of the sensor mat of FIG. 1 with the trim removed from the seat bottom to reveal the sensor mat.
Figure 6:
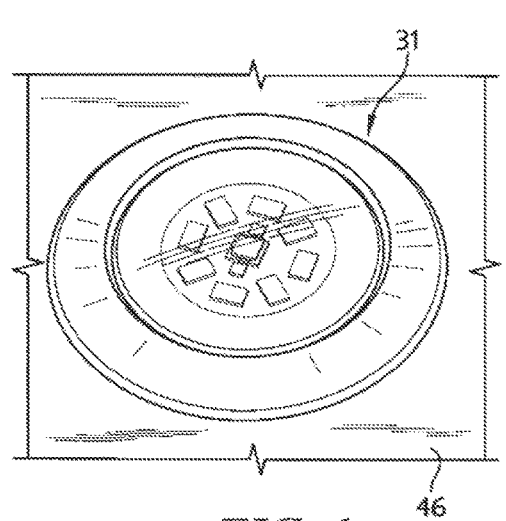
FIG. 6 is an enlarged partial perspective view of the oximetry sensor of FIG. 1 showing that the oximetry sensor includes eight LED emitters positioned to lie around a central light receiver.
Figure 7:
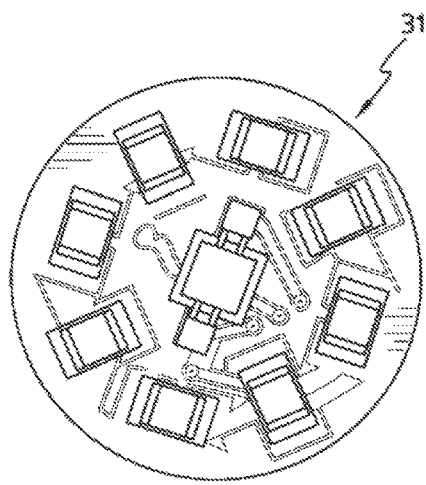
FIG. 7 is a photograph of the oximetry sensor of FIG. 1 separated from a sensor mount and a sensor shield removed to expose underlying circuitry included in the oximetry sensor.

Oximetry sensor system 20 includes a first oximetry sensor 31 and a second oximetry sensor 32 as shown in FIGS. 1 and 8. Oximetry sensors 31, 32 are coupled to seat bottom 12 as shown in FIGS. 1, 3, and 6. Oximetry sensors 31, 32 are spaced apart from one another and spaced apart from ECG mat 28 as shown in FIG. 1. Each oximetry sensor 31, 32 is arranged to underlie an associated leg of the occupant and is arranged to sense oxygen content in the occupant's blood. Each oximetry sensor 31, 32 emits light at a wavelength which passes through clothing layers 41, 42, 43N and enters occupant's skin 40 where a portion of the light is absorbed by the occupant's blood. The remaining portion of the light is reflected by the occupant's blood back through clothing layers 41, 42, 43N and is detected by each oximetry sensor 31, 32. The detected light is converted to an oximetry signal and sent to control system 22.

With regard to oximetry sensors 31, 32, and for purposes of background, oxygen saturation refers to oxygenation, or when oxygen molecules ($O_2$) enter the tissues of the human body. In the human body, blood is oxygenated in the lungs, where oxygen molecules travel from the air and into the blood. Oxygen saturation, also called $O_2$ sats, is a measure of the percentage of hemoglobin binding sites in the bloodstream occupied by oxygen. Measurement of a subject's oxygen saturation provides one indication of the subject's overall health and, more particularly, the subject's pulmonary and cardiovascular health as both the pulmonary and cardio-vascular systems cooperate with each other and other systems of the human body to perform oxygenation. Arterial oxygenation is measured typically using pulse oximetry, which is a non-invasive technology for monitoring the saturation of a subject's hemoglobin.

In transmissive pulse oximetry techniques, a sensor is placed on a thin part of a subject's body, for example, a fingertip or earlobe, or in the case of an infant, across a foot. Light of two different wavelengths is passed through the subject's tissue to a photodetector. The changing absorbance at each of the wavelengths is measured, allowing determination of the absorbances due to the pulsing arterial blood alone, excluding venous blood, skin, bone, muscle, and fat. Another type of pulse oximetry is reflectance pulse oximetry. Reflectance pulse oximetry may be used as an alternative to transmissive pulse oximetry described above. Reflectance pulse oximetry does not require a thin section of a subject's body. Therefore, reflectance pulse oximetry is better suited to more universal application such as measurement of blood oxygen concentration in the feet, forehead, and chest. However, reflectance pulse oximetry also has some limitations.

Pulse oximetry is based on the principal that oxy- and deoxy-hemoglobin have different light absorption spectra. Reflective pulse oximetry measures the light absorption of light of two different wavelengths via reflectivity; that is, by knowing the amount of light transmitted and detecting the amount of light reflected using a photodector or similar sensor, one is able to determine the amount of light absorbed by the subject's body, i.e., the light absorption. However, the efficacy of non-contact pulse oximetry through intervening materials is subject to the absorption spectra of those materials.

In one embodiment, oximetry sensors 31, 32 are oximetry sensors, also called PulseOx sensors, which are configured to determine blood oxygenation through a variable makeup of intervening materials, and are configured with the ability to switch between or select from multiple wavelengths of light to be transmitted at the subject's body. Based on the reflected amount of light resulting from the various wavelengths, the sensor assembly is able to select one or more optimum wavelengths of light to be transmitted at the subject's body to determine the oxygen saturation for the subject via reflective pulse oximetry. One exemplary oximetry sensor is disclosed in U.S. Provisional Patent Application Ser. No. 61/730,374 filed Nov. 27, 2012, the contents of which is incorporated by reference in its entirety herein.

FIG. 18 is a schematic diagram illustrating electronic components of a sensor assembly provided in accordance with disclosed embodiments. As shown in FIG. 18, at least one disclosed embodiment of the sensor assembly 400 includes three exemplary stages: a photodetector stage 405, an input/output and processing stage 415 and a light emission stage 430. Photodetector stage 405 includes a photodetector or photodiode 410 that is used to detect reflected amounts of light from a subject's body. Photodetector stage 405 also includes various circuitry elements that enable buffering and filtering of the detected signal including operational amplifiers for establishing a virtual ground and buffering and filtering of the signal output from the photodetector 410.

The teachings of U.S. Pat. No. 5,348,004, entitled "Electronic Processor for Pulse Oximeter" and U.S. Pat. No. 6,839,580, entitled "Adaptive Calibration for Pulse Oximetry" are both hereby incorporated by reference herein in their entirety. Each of those patents disclose various equipment, components, and methodology that may be used to implement the disclosed embodiments for sensing and monitoring blood oxygen in a seating environment.

The output of photodetector stage 405 is coupled to the input/output and processing stage 415 so as to enable analysis of the signal detected by the photodetector to perform calibration of the sensor assembly and detection and monitoring of the subject's blood oxygen content. The input/output and processing stage 415 includes a communication bus 420 that couples the sensor assembly components of stages 405 and 430 with the processor 425. This coupling and associated bidirectional communication enables the processor 425 to control emission of light via the light emission stage 430 and receive reflected signals from the photodetector stage 405 to perform processing for calibration, detection, and monitoring of the subject's blood oxygen content.

Light emission stage 430 includes one or two banks of LEDs, 435, 440. The LED banks may be optimized to use off-the-shelf LEDs at, for example, 850 nm and 950 nm light that penetrate a wide range of materials well. The light emission stage 430 may use additional or alternative banks of LEDs, for example, at additional wavelengths between 600 nm and 1100 nm for greater robustness of signal to noise determination. In implementation, the stages illustrated in FIG. 18 and the incorporated components are selected from commercially available electronics components listed in the table of FIG. 19. Further, it should be noted that the photodiode 410, i.e. the receptor, and the LEDs of the LED banks 435, 440, i.e., the emitter, may be approximately 7.5 mm to avoid spill over from the LEDs to the photodiode.

Embodiments disclosed herein provide the ability to perform noninvasive, non-distracting monitoring of blood oxygen contact through multiple layers of material. A calibration sub-routine for sensor and sensor assembly learns the best light components for a particular subject being monitored. This is because the light components used for reflective monitoring change depending on the amount, type, and number of impeding barriers, such as clothing layers discussed herein, for a particular subject. Thus, disclosed embodiments may use custom designed circuitry developed to read PulseOx (also known as photoplesythmography, or PPG) signals through variable layers of intervening clothing worn by a subject. Thus, disclosed embodiments enable sensor assembly calibration cycling through multiple wavelengths of light to enable a spectral analysis of materials and oxy/deoxy-hemoglobin absorption to ascertain optimal wavelengths for material penetration and determination of oxygen saturation curves while maximally identifying movement and other artifacts.

Disclosed embodiments of the sensor assembly may also be configured to perform auto-calibration, which enables the ability to penetrate an unknown makeup of intervening material to read changes in reflected light that accompany fluctuations in oxy- and deoxy-hemoglobin accompanying each heartbeat. Because some of the relevant aspects of PulseOx signals change at very slow time-scales (e.g., respiration changes 10+ seconds), simply using high-pass filtering of the signal merely creates substantial distortions and delays. To avoid the problems of high-pass filters, custom circuitry and algorithms were developed, and are disclosed in U.S. Provisional Patent Application Ser. No. 61/730,374, which is expressly incorporated by reference herein.

Referring back to FIG. 8, control system 22 is configured to communicate with each oximetry sensor 31, 32 to command each oximetry sensor 31, 32 to execute an auto-calibration process each time an occupant sits on vehicle seat 10. The auto-calibration process causes the amount of light emitted from oximetry sensors 31, 32 to be varied. In on example, high-frequency pulse width modulation is used to vary the light being emitted. However, a digitally controlled potentiometer may also be used. Light levels are increased in a stepped manner until sufficient light is reflected back from occupant's skin through multiple layers of clothing. Each time an occupant sits on vehicle seat 10, the number of layers and type of layer may change. As a result, the amount of light required to pass through the clothing layers, be reflected from the occupant's skin, and pass back through the clothing layers to provide an indication of oxygen content in the occupant's blood also may change. The auto-calibration process causes the light output to gradually increase until a sufficiently strong signal is returned without causing the oxygen content to be drowned out by excess light.

Oximetry sensors 31, 32 are coupled to a seat cushion 44 included in seat bottom 12 and surrounded by trim 46 as shown in FIG. 3. Oximetry sensors 31, 32 are configured to detect oxygen content in an occupant's blood through first, second, and Nth clothing layers 51, 52, and 53N as shown in FIG. 3. In one example, first clothing layer 51 is a pair of pants made from denim. Second clothing layer 52 is a pair of underpants made from cotton. Nth clothing layer 53N may be a pocket included in the pair of pants or any other suitable alternative. Nth clothing layer 53N may be one layer or multiple layers.

Control system 22 includes an analog to digital converter 48, a computer 54, and an output 56 as shown in FIG. 8. Once the oximetry signals and the ECG signal are obtained, the analog signals are then converted to digital signals by analog to digital converter 48. The digital signals are then processed by computer 54. The signals may be processed by computer 54 to determine a heart rate 61, blood pressure 62, respiration rate 63, and stress level 64 as shown in FIG. 1. Processes for determining heart rate 61, blood pressure 62, respiration rate 63, and stress level 64 are shown in FIGS. 9-14. Computer 54 and underlying processor(s) may be based on any of a suitable family of instruction set architectures for computer processors, such as ARM, x86, or any other reduced instruction set computing (RISC) architecture.

Processors and processor platforms for computer 54, as well as for any processor-based device disclosed herein, may be embodied as microcontrollers (MCUs). In certain illustrative embodiments, MCUs may be equipped with on-chip embedded Flash memory in which to store and execute programs for performing any suitable function described herein. By storing at least some of the programs, the MCU may advantageously have a very short start-up period and can be executing code very quickly. They may also utilize external memory to provide program and data storage.

An ECG-signal acquisition process 70 is shown, for example, in FIG. 9. ECG-signal acquisition process 70 includes the steps of obtaining 71 electrical signals from occupant 50, transforming 72 the electrical signals in ECG unit 30, passing 73 signals through ECG mat 28, passing 74 the signal through occupant 50, converting 75 the analog signal to a digital signal, and filtering 76 the signal to provide an ECG signal for use by computer 54. Computer 54 uses the ECG signal to determine heart rate 61, heart-rate variability 65, stress level 64, a pulse-transit time 66, and blood pressure 62 as shown in FIG. 9. ECG signal 58 is obtained when first and second ECG receivers 24, 26 sense electrical signals in occupant 50. Based on the output of the processing, computer 54 may perform a predetermined action. The predetermined action may be storing the calculated values in memory 542 of computer 54. The predetermined action may be activating output 56 to communicate the output to the occupant.

Obtaining step 71 obtains electrical signals from occupant 50 as shown in FIG. 8. ECG receivers 24, 26 sense electrical signals from occupant 50. Those sensed electrical signals are then passed (1) to ECG unit 30 which are then passed (2) through ECG mat 28 which communicates (3) the signals back to occupant 50. First and second ECG receivers 24, 26 then sense (4) the signal a second time which has been cleaned and amplified. The signal is once again communicated (1) to ECG unit 30 which then communicates (5) the signal to analog to digital converter 48 as shown in FIG. 8.

An oximetry signal acquisition process 80 is shown, for example, in FIG. 10. Oximetry signal acquisition process 80 includes the steps of obtaining 81 oximetry signals from occupant 50, converting 82 the analog signals to digital signals, filtering 83 the digital signals to remove noise, and determining 84 the best oximetry signal from the two oximetry sensors 31, 32. Computer 54 uses the oximetry signal to calculate pulse-transit time 66, blood pressure 62, respiration 67, a respiration rate 68, and respiration depth 69 as shown in FIG. 10. Oximetry signal 60 is obtained when first and second oximetry sensors 31, 32 sense oxygen content in occupant's blood. Based on the output of the processing, computer 54 may activate output 56.

Obtaining step 81 obtains oximetry signals from occupant 50 as shown in FIG. 8. In a first sub-step, each oximetry sensor 31, 32 emits (1) light which passes through the occupant's clothing and passes into occupant 50. A portion of the light is then reflected (2) back from occupant 50 and captured by each associated oximetry sensor 31, 32. Each oximetry sensor 31, 32 then takes the captured light and coverts (3) it to a signal which is then communicated to analog to digital converter 48 as shown in FIG. 8.

Heart rate 61 is calculated by computer 54 using heart-rate determination process 90 as shown in FIG. 11. Heart-rate determination process 90 includes the steps of detecting 91 heart beats from the ECG signal, differentiating 92 the heart-beat signal, determining 93 a raw heart rate, determining 94 reliability of each signal, weighing 95 more reliable signals, and calculating 96 an average heart rate (FIG. 10, ref. 61). Detecting step 91 detects heart beats by using threshold and peak detection of ECG signal 58. Determining step 94 determines the reliability of each signal. In one example, determining step 94 uses peak analysis to remove erroneous data, the root mean square of the signal to determine stronger signals, and signal to noise ratio to determine more reliable signals. Once heart rate data is determined from 90, further determinations may be made regarding heart-rate variability 100 and stress level 110, discussed below.

Once heart rate 61 is determined by computer 54 in heart-rate determination process 90, computer 54 may then proceed to a heart-rate variability determination process 100 as shown in FIG. 12. Heart-rate variability determination process 100 includes taking 101 a derivative of the heart rate, determining 102 heart rate variability spectrum by taking a Fourier transform of the signal, determining 103 a ratio of high frequencies to all frequencies, and determining 104 the impact of adrenaline on the occupant. Adrenaline affects the lower frequencies of heart rate variability. As a result, if the lower frequencies are driving heart rate variability, computer 54 may proceed to stress-determination step 110 as shown in FIG. 12. In stress-determination step 110, computer 54 identifies that the occupant is under stress when adrenaline is increasing.

Determining step 103 includes calculating a ratio of high frequencies to all frequencies. As an example, LF is the power contained in low frequencies (0.05-0.125 Hz) and HF is the power contained in high frequencies (0.2-0.3 Hz).

$$LH2HF\ ratio = \frac{LF}{(LF + HF)}$$

$$Emotional\ Stress = \sqrt{\frac{LF}{(LF + HF)}}$$

In this example, as the value approaches zero percent, an occupant's stress level is the lowest. As the value approaches 100 percent, the occupant's stress level is the highest.

Computer (54) may combine ECG signal 58 and oximetry signal 60 to obtain pulse-transit time 66 and blood pressure 62 as shown in FIG. 13. Computer (54) performs a pulse-transit time determination process 120. Pulse-transit time determination process 120 includes the steps of detecting 121 peaks in ECG signal 58, detecting 122 peaks in oximetry signal 60, determining 123 time between peaks in oximetry signal 60, and calculating 124 pulse-transit time 66. Once pulse-transit time 66 is determined by computer 54, computer 54 proceeds to a blood-pressure determination process 130 as shown in FIG. 13. Blood-pressure determination process 130 includes the steps of transforming 131 pulse-transit time 66, estimating 132 systolic blood pressure, and estimating 133 diastolic blood pressure as shown in FIG. 13.

Blood-pressure determination process 130 may be further improved by adding an occupant's anthropomorphic data into the calculation. Specifically, knowledge about a distance between an occupant's heart and the location on the occupant's leg where one of the oximetry sensors is taking a measurement could improve accuracy. Faurecia's SMARTFIT® technology may be used to provide such anthropomorphic data to computer 54.

Computer 54 may use only oximetry signal 60 to determine respiration rate 68 and respiration depth 69 as shown, for example, in FIG. 14. Computer 54 performs a respiration-rate determination process 140 that includes the steps of detecting 141 valleys in oximetry signal 60, detecting 142 peaks in oximetry signal 60, determining 143 time between the peaks, calculating 144 respiration rate 68, and determining 145 amplitude difference between peaks and valleys as shown in FIG. 14. Once the amplitude difference is determined, computer 54 may proceed to calculating 146 respiration depth 69. Respiration rate 68 and respiration depth 69 may be useful in determine an emotional state of occupant 50, awareness of occupant 50, alertness of occupant 50, and other suitable health and/or physiological indicators.

Computer 54 executes the various processes described above using a processor 541 included in computer 54 as shown in FIG. 15. The processes 70, 80, 90, 100, 110, 120, 130, and 140 are stored, for example, in memory 542 of computer 54 which is coupled to processor 541. Computer 54 further includes inputs 543 and power supply 544. Inputs 543 are arranged to interconnect processor 541 and analog to digital converter 48 so that ECG signal 58 and oximetry signal 60 may be communicated to processor 541 for processing. Processor 541 is further coupled to output 56 as shown in FIGS. 8 and 15. Power supply 544 is coupled to processor 541 and configured to provide power to processor 541 and memory 542.

In one example, computer 54 is located in vehicle seat 10 and coupled to a controller area network included in the vehicle. In another example, computer 54 is located in spaced-apart relation to vehicle seat 10 and may be a computer which controls other equipment in the vehicle. In either example, output 56 may be used to provide audio, visual, or tactile feedback.

In one example, output 56 may be a video screen located in the vehicle which provides output from computer 54 and receives input from the occupant. Such input may be captured through one of inputs 543 and communicated to processor 541 for further processing. In another example, output 56 may also be an instrument panel included in the vehicle. In another example, output 56 may be a personal computer, a mobile device or smart phone, or communication device which sends data provided by processors 541 remotely. Data may be sent remotely to a doctor, a vehicle manufacturer, or any other suitable alternative. In the example of a doctor, the data may be used to prescribe treatments which may be performed with or without the vehicle seat. In another example, output 56 may be an actuator included in vehicle seat 10 which moves portions of vehicle seat 10. In this example, the actuator may be use to adjust an angle at which seat back 14 extends upwardly away from seat bottom 12.

Electronics system 16 obtains sensor data from signals obtained and computer 54 processes the signals to obtain information related to occupant 50. Electronics system 16 may cooperate with seat bottom 12, seat back 14, other vehicle systems, and systems separate from the vehicle to maximize occupant comfort, maximize occupant capacity to control the vehicle, maximize occupant health, and maximize the emotional well being of the occupant.

Additional information relating electronics systems in accordance with the present disclosure may be found in U.S. Provisional Patent Application Ser. No. 61/846,871 filed Jul. 16, 2013, U.S. Provisional Patent Application Ser. No. 61/730,349 filed Nov. 27, 2012, and International (PCT) Patent Application Serial No. PCT/US2013/071620 filed Nov. 25, 2013, all of which are expressly incorporated by reference herein Occupant comfort may be maximized according to several exemplary modes such as an auto-fit mode, a smart-memory mode, a pro-active comfort mode, a pro-active thermal-adjustment mode, a next-position mode, a comfort-validator mode, a smart-massage mode, a targeted heating and cooling treatment mode, a recommended break-activity mode, a better circulation mode, a tension relief mode, an energize mode, and an arrival coach mode.

An auto-fit mode may use sensor data collected by electronics system 16 and other data communicated to computer 54 via input 543 to change the position and orientation of vehicle seat 10 and other components in the vehicle automatically. As a result, the occupant's comfort is maximized according their physiological data.

A smart-memory mode may use sensor data collected by electronics system 16 to determine an identity of the occupant and save settings of vehicle seat 10 according to the identity of the occupant. As a result, the electronics system 16 may position vehicle seat 10 and vehicle equipment according to the stored profile of the occupant associated with the identified identity.

A pro-active comfort mode may use sensor data collected by electronics system 16 to predict physical or thermal discomfort and make changes in response. Changes may occur before the occupant recognizes physical or thermal discomfort. The sensor data may be processed by computer 54 and compared with known or learned trends to predict physical or thermal discomfort. Computer 54 may learn that when certain sensor data occurs, an occupant manually performs an action such as turn down a blower included in the vehicle's HVAC system.

The pro-active thermal-adjustment mode may use sensor data collected by electronics system 16 to predict thermal discomfort and make changes in response. In one example, electronics system 16 may sense of thermal discomfort on an occupant's face and command via output 56 the vehicle's Heating, Ventilation, and Air Conditioning (HVAC) system to provide reduced heating or cooling only to the occupant's face.

A next-position mode may use sensor data collected by electronics system 16 to calculate a new arrangement of the vehicle seat based on known physiological data such as the dimensions of an occupant's body parts. As a result, computer 54 through output 56 commands vehicle seat 10 to make adjustments in position and orientation to further maximize patient comfort according to real-time sensor data.

A comfort-validator mode may use sensor data collected by electronics system 16 to determine if changes made by computer 54 via output 56 have resulted in objective measures of improved comfort. As a result, an occupant may determine if their comfort has actually improved as compared to whether they think it has improved.

A smart-massage mode may use sensor data collected by electronics system 16 and output 56 to provide constantly improving treatments to a specific occupant's stress and fatigue. In one example, a first massage algorithm may be established to treat an occupant. During the trip, the electronics system 16 may determine that a second different massage algorithm should be established to further mitigate the occupant's stress and fatigue.

A targeted heating and cooling treatment mode may use sensor data collected by electronics system 16 and output 56 to command the vehicle's Heating, Ventilation, and Air Conditioning (HVAC) system to provide localized heating or cooling to the occupant. As a result, energy used to provide thermal comfort to the occupant is minimized while occupant comfort is maximized.

A recommended break-activity mode may use sensor data collected by electronics system 16 before a break from travel is taken by the occupant and after a break is taken from travel by the occupant to determine the most effective break activities for use by the occupant. As an example, computer 54 may learn over time that when the occupant drives for at least two hours, the most effective break activity for the occupant is a specific stretching routing by comparing sensor data obtained before and after other break activities. In addition, computer 54 may determine that the previously performed break activities were insufficient and prescribe new break activities by monitoring post-break sensor data.

A better circulation mode may use sensor data collected by the electronics system 16 to determine that blood flow in one or more locations of an occupant is or may soon be poor. In one example, the oximetry sensors in the seat may be used by computer 54 to determine trends relating to blood flow. As a result, computer 54 may command through outputs 56 various features of the vehicle and vehicle seat to engage and maximize circulation in the occupant. In one example, computer 54 may command massage to be provided by the vehicle seat. In another example, computer 54 may command the vehicle seat to actuate changing and orientation of the vehicle seat to promote increased circulation. In yet another example, computer 54 may command heat to be applied to the occupant by the vehicle seat. In yet another example, computer 54 may suggest that a break be taken by the occupant and one or more break activities (e.g., stretching, walking, etc.) by the occupant.

A tension relief mode may use sensor data collected by the electronics system 16 to determine a tension level of an occupant. In one example, tension may be characterized as a measure of muscle tension of the occupant. Muscle tension may be determined from inputs such as stress, posture, and pressure exerted on the occupant. In one illustrative scenario, computer 54 may determine that an occupant is experiencing high tension. As a result, computer 54 may ask the occupant if the occupant wants to decrease sensed tension through use of one or more features. In another example, computer 54 may detect increased tension and automatically engage one or more features to minimize the occupant's tension.

In one example, computer 54, via output 56, may command massage to be provided by the vehicle seat. Various characteristics of massage may be varied by computer 54 to minimize tension such as frequency, intensity, location, and patterns of application to the occupant.

In another example, computer 54 may command application of heat or cooling to the occupant using the vehicle seat and or the vehicle heating and cooling systems to minimize tension. Various characteristics of heating and cooling include location of application, temperatures applied, duration, and patterns of application to the occupant. Patterns of application may include alternating hot and cold or slowly increasing hot or cold intensity.

In yet another example, computer 54 may command air flow in the cabin of the vehicle to be altered to minimize tension. In one example, cabin windows may be lowered to permit air from outside the vehicle to blow into the cabin. In another example, computer 54 may command pressurized air to be blown onto specific locations of the occupant with varying amounts of pressure, volume, and temperature.

In yet another example, computer 54 may command one or more characteristics of lighting in the vehicle to change to minimize tension. Various characteristics of lighting including location, color, wavelength, intensity, and duration of lighting.

In still yet another example, computer 54 may use music to minimize tension. Specifically, computer 54 may over time monitor how various music types influence tension in the occupant. As a result, computer 54 may determine that various music types minimize tension and play those types of music when tension is found to be high in the occupant.

In another example, computer 54 may engage various scents to be deployed to the cabin of the vehicle. The scents may be tied to known aroma therapies which are believed to minimize tension when applied to an occupant.

In still yet another example, computer 54 may provide commands to the occupant regarding suggested movements to minimize tension. In one illustrative example, computer 54 may detect increased tension and provide commands to the occupant to perform one or more stretching routines to minimize tension.

A tension ease mode may use various combinations of functions discussed above in tension relief mode. In one example, computer 54 may combine massage which is robust and intense in both the seat cushion and the seat back to be combined with lower levels of heat to be applied to the area having increased tension.

An energize mode may use sensor data collected by the electronics system 16 to determine an energy level of an occupant. In one example, computer 54 may use several inputs to determine the occupant's energy level. These inputs include: vehicle-based measures, behavioral measures, and physiological measures. Vehicle-based measures include counting a number of deviations from desired lane position and monitoring for changes in movement of a steering wheel and pressure on an accelerator pedal or brake pedal that deviate significantly from previously monitored normal use. Behavioral measures may be monitored through a camera in the cabin and include, for example, yawning, eye closure, eye blinking, and head position. Physiological measures include correlations between ECG signal, Electromyogram (EMG), eletrooculogram (EoG), and EEG may be used to determine drowsiness or low energy level of the occupant.

In one illustrative scenario, computer 54 may determine that an occupant has low energy. As a result, computer 54 may ask the occupant if the occupant wants to increase sensed energy through use of one or more features. In another example, computer 54 may detect decreased energy and automatically engage one or more features to increase the occupant's energy based on the occupant's location or schedule.

In one example, computer 54 via output 56 command massage to be provided by the vehicle seat. Various characteristics of massage may be varied by computer 54 to maximize energy of the occupant such as frequency, intensity, location, and patterns of application to the occupant. In addition, computer via output 56 may also simulate various yoga-like postures through changing an arrangement of the vehicle seat to support and suggest the yoga-like posture.

In another example, computer 54 may command application of heat or cooling to the occupant using the vehicle seat and or the vehicle heating and cooling systems to maximize energy of the occupant. Various characteristics of heating and cooling include location of application, temperatures applied, duration, and patterns of application to the occupant. Patterns of application may include alternating hot and cold or slowly increasing hot or cold intensity.

In yet another example, computer 54 may command air flow in the cabin of the vehicle to be altered to maximize energy of the occupant. In one example, cabin windows may be lowered to permit air from outside the vehicle to blow into the cabin. In another example, computer 54 may command pressurized air to be blown onto specific locations of the occupant with varying amounts of pressure, volume, and temperature.

In yet another example, computer 54 may command one or more characteristics of lighting in the vehicle to change to maximize energy of the occupant. Various characteristics of lighting including location, color, wavelength, intensity, and duration of lighting.

In still yet another example, computer 54 may use music to maximize energy of the occupant. Specifically, computer 54 may over time monitor how various music types influence energy level in the occupant. As a result, computer 54 may determine that various music types maximize energy of the occupant and play those types of music when energy level is found to be low in the occupant.

In another example, computer 54 may engage various scents to be deployed to the cabin of the vehicle. The scents may be tied to known aroma therapies which are believed to maximize energy of the occupant when applied to an occupant.

In still yet another example, computer 54 may provide commands to the occupant regarding suggested movements to maximize energy of the occupant. In one illustrative example, computer 54 may detect decreased energy and provide commands to the occupant to perform one or more stretching routines to maximize energy.

A blood flow mode may use sensor data collected by electronics system 16 to determine whether blood flow is being inhibited or is likely to be inhibited during a trip. In one example, sensor data may indicate that blood flow is currently sufficient, but computer 54 may examine route information and determine that blood flow is likely to be problematic at some time in the future due to limited opportunities to exit the interstate and walk around increasing blood flow. As a result, computer 54 may command for gentle heat to be applied form the cushion and for gentle massage to be applied to promote increased blood flow.

An arrival coach mode may use sensor data collected by the electronics system 16 to determine what state of mind the occupant should be at for a specific location or time of day. In one example, electronics system 16 may use Global Positioning System (GPS) data to determine a location of a vehicle and automatically engage one or more of the above mentioned modes so that the occupant is in the appropriate state of mind for the location. In one scenario, the electronics system 16 may determine the vehicle is approaching the occupant's home at the end of the day and that the occupant has high tension. As a result, computer 54 may engage the tension relief mode to minimize tension of the occupant. In another example, electronics system 16 may determine from an occupant's calendar that a work meeting is coming up shortly and the occupant's energy level is low. As a result, computer 54 may engage the energize mode to cause the occupant's energy level to increase in preparation for attending the meeting.

In one example, specific locations and meeting types may be programmed by the occupant for use with the arrival coach mode. In another example, the computer 54 may automatically determine through various factors that certain locations lead to increase tension and other locations lead to decreased tension. As a result, computer 54 may attempt to automatically raise the energy level of the occupant when entering high tension locations and decrease tension of the occupant when entering low tension locations.

Occupant capacity for operating the vehicle may be maximized according to several exemplary modes. Those modes include a driver-capability assessment mode, a behavior-coach mode, a check-in on mode, a time to see doctor mode, an attack alert mode, an attach-coach mode, and a right responder mode.

A driver-capability assessment mode may use sensor data collected by electronics system 16 to determine if the driver's capability to operate the vehicle is impaired due to overload, fatigue, drowsiness, stress, and alcohol or drug impairment. As a result, computer 54 may command via output 56 various equipment in the vehicle to communicate to the driver that their capability is impaired. Computer 54 may also take command of the vehicle to slow the vehicles speed or call for assistance.

A behavior-coach mode may use sensor data collected by electronics system 16 to determine an impact of the occupant's behavior of their capacity to operate the vehicle. As an example, computer 54 may log an incoming phone call followed by a spike in heart rate because the occupant was distracted by the phone call and surprised by changing road conditions. Thus, computer 54 may remind the occupant that various activities have caused distraction before.

A check-in on mode may use sensor data collected by electronics system 16 to determine that the occupant is operating at full capacity. In one example, computer 54 may communicate sensor data via output 56 to a remote person showing the remote person that the occupant is operating at a sufficient capacity. In this example, the occupant may be an elderly occupant the remote person may be a family member.

A time-to-see-doctor mode may use sensor data collected by electronics system 16 to determine that sensed data is indicative that a visit to the doctor is warranted. As an example, the computer 54 may determine that the occupant's blood pressure has been sufficiently high for several days. As a result, computer 54 may via output 56 communicate a suggestion to the occupant to visit with their doctor.

An attack alert mode may use sensor data collected by electronics system 16 to determine that the occupant is suffering from a medical attack such as a heart attack. As a result, computer 54 may command via output 56 that medical personnel or a family member contacted. Computer 54 may also cause the vehicle to be slowed and stopped and the hazard lights to be turned on.

An attach-coach mode may use sensor data collected by electronics system 16 to determine that the occupant is suffering from a medical attack such as a heart attack. As a result, computer 54 may communicate instructions via output 56 to the occupant which causes the occupant to respond to the attack in an optimal way. In one example, computer 54 may communicate to the occupant the need to slow down, pull over, and call for assistance.

A right responder mode may use sensor data collected by electronics system 16 to determine that the occupant's biometric data at the time of and after an accident. The occupant's actual biometric data may then be communicated by electronics system 16 to first responders so that the first responders are better prepared to treat the occupant. In another illustrative example, the electronics system 16 may store the occupant's biometric data over time. Once an accident occurs, the electronics system 16 may send both the historical biometric data and the biometric data from and after the accident to the first responders. In this example, the first responders are able to determine what biometric data is related to the accident rather than typical of the occupant. In yet another example, electronics system 16 gathers known medical data about the occupant and sends the known medical data to first responders along with the biometric data from the crash. In this example, first responders may be notified of an allergy or other medical information relevant to the occupant.

The occupant's emotional well being may be maximized according to several exemplary modes. Those modes include an alter-environment mode, a stress-mapper mode, a task-manager mode, an emotional-geotagging mode, and a mood-optimized playlist mode.

An alter-environment mode may use sensor data collected by electronics system 16 to change the environment of the occupant to maximize emotional well being. In one example, computer 54 may analyze collected sensor data to determine that a change in sound emitted from the vehicle's sound system would improve the emotional well being of the occupant.

A stress-mapper mode may use sensor data collected by electronics system 16 as well as other data collected by the vehicle to determine whether geographical locations and/or routes caused increased stress. As a result, computer 54 may be able to correlate specific locations, traffic patterns, and routes with increased stress and recommend alternatives to minimize stress.

A task-manager mode may use sensor data collected by electronics system 16, other data available from vehicle systems, and data provided by smart devices to determine an optimal arrangement of tasks to be completed. As a result, computer 54 may via output 56 suggest changes to the occupant's schedule, route, media, and phone to maximize productivity while minimizing stress.

An emotional-geotagging mode may use sensor data collected by electronics system 16 and other data, such as location data, provided by the vehicle to tie location with emotional state. In addition, the computer 54 may combine emotional data with communications received and recorded by the vehicle along with location. As a result, computer 54 may learn that various factors which influence the emotional state of the occupant.

A mood-optimized playlist mode may use sensor data collected by electronics system 16 to change the music playlist provided by the sound system of the vehicle. Computer 54 may map emotional state with songs played to determine a response which organizes songs to provide a therapy which minimizes stress. Computer 54 may monitor sensor data to confirm that the mood-optimized playlist is having the intended function and make changes in response to the sensor data obtained.

An occupant's health may be maximized according to several exemplary modes. Those modes include a health-metric gathering mode, a health-metric tracking mode, a health-metric sharing mode, a workout-optimizer mode, a destination-prep mode, and a posture coach mode.

A health-metric gathering mode may use sensor data collected by electronics system 16 to gather and store various health metrics like heart rate, blood pressure, and respiration rate. As a result, computer 54 may provide upon request stored or real-time health metrics about the occupant.

A health-metric tracking mode may use sensor data collected by electronics system 16 to track changes in health metrics over time by storing processed sensor data in memory 542 of computer 54 or communicating processed sensor data to a party remote from vehicle seat. As a result, health metrics may be viewed over a period of time.

A health-metric sharing mode may use sensor data collected by electronics system 16 to provide health metrics which may be shared intermittently or continuously with a third party. Computer 54 may via output 56 communicate to a doctor, for example, heart rate information collected over a period of time.

A workout-optimizer mode may use sensor data collected by electronics system 16 to determine a workout routine which arranges a workout to accomplish the occupants goals. In one example, the occupant may wish to maximize muscle gain and computer 54 may arrange a workout which maximizes muscle gain by sensing which muscles will benefit most from a workout and providing exercises which accomplish this result. Computer 54 also may analyze pre-workout sensor data and post-workout sensor data to determine if the workout was optimal. Computer 54 may also optimize an occupant's workout to maximize the occupant's metabolism.

A destination-prep mode may use sensor data collected by electronics system 16 and other data provided to computer 54 to prepare the occupant for their arrival at their destination. As a result, the occupant may be able to take steps which allow them to be in the best position to arrive at their destination. As an example, computer 54 may determine from sensor data that the occupant is drowsy and suggest that coffee or food may be beneficial prior to arrival so that the occupant is awake.

A posture coach mode may use sensor data collected by electronics system 16 to determine that the occupant's current posture while sitting on vehicle seat 10 could be improved. Computer 54 may provide via output 56 suggestions to the occupant of how to improve the occupant's posture along with benefits that may come from changes in posture such as improved mood, increased blood flow to certain areas of the back, reduced back pain, and better visibility.

A breathing coach mode may use sensor data collected by electronics system 16 other data provided to computer 54 to coordinate breathing of an occupant so that a desired outcome is achieved such as reduction in stress, increased calmness, increased oxygen content in the body, improved alertness, etc. In one example, computer 54 may cause the vehicle seat to define a breathing rhythm for the occupant by inflating a lumbar air bladder to suggest inhaling and deflating the lumbar air bladder to suggest inhaling. In another example, computer 54 may cause the vehicle seat to define a breathing depth by coordinating inflation of multiple bladders included in a seat back of the vehicle seat. Bladders may inflate in sequence from a bottom of the seat back to a top of the seat back to indicate depth and length of inhale. Similarly, bladders may deflate in sequence from top to bottom to indicate exhale. In another example, other seat functions such as linear or mechanical actuators may be used to communicate to the occupant how to breathe. In still yet another example, motor pulsing and massage may be used to communicate to the occupant how to breathe.

Usability and value of the vehicle may be maximized according to several exemplary modes. Those modes include an identification mode and an insight mode.

An identification mode may use sensor data collected by electronics system 16 to determine an occupant's identity. Computer 54 may examine various signals collected by electronics system 16 and use features of those signals to identify an occupant. In one example, time domain features may be extracted from the ECG signal and used to identify an occupant. In one example, computer 54 may collect data such as heart rate and breath rate and associate that data with a specific occupant based on features of the ECG signal currently being received by computer 54. As a result, the data collected by the computer 54 is associated and stored with the appropriate user. As a result, biometric history stored and transferred to a healthcare provider or first responder is confirmed to belong to the occupant.

Once the identification of the occupant is known, computer 54 may perform various activities. In one example, computer 54 tracks an occupant's behaviors such as selecting various modes of operation along with times and location. In addition, computer 54 also tracks an occupant's biological response to those behaviors and actions to determine if more appropriate actions should be recommended next time or changes to the modes of operation should be made to obtain more desirable effects.

In another example, computer 54, when the occupant's identification is known, may also begin customizing modes of operation according to a specific occupant's preferences and known responses to modes of operation begins to track behavior of the occupant. In addition, computer 54 may communicate with an external device (e.g., FuelBand™, FitBit™ mobile phones, tablet computers, personal computers medical devices) to add additional information to an occupant's stored profile.

One example of operation is when an occupant is wearing an activity monitoring device and has been sitting at his or her desk with little activity for the previous eight hours. Once the occupant sits on the vehicle seat, computer 54 begins communicating with the activity monitoring device and understands the occupant has had little activity all day. As a result, the suggested mode of operation is customized (e.g., upright seat and vigorous massage) to the previous activity.

In a comparative example of operation, the occupant is wearing an activity monitor and has just completed a strenuous workout at the gym. Once the occupant sits on the vehicle seat, computer 54 begins communicating with the activity monitoring device and understands the occupant has just been very energetic. As a result, the suggested mode of operation is customized (e.g., reclined seat back, light massage, and low heat) to the previous activity.

In yet another example of operation, computer 54, when the occupant's identity is known to computer 54, coordinates music selection and play back with a computer included in the vehicle associated with music play back. Computer 54 may use ECG sensors, Pulse Ox sensors, and GSR sensors to determine an emotional state (e.g., stress) of the occupant when listening to different songs. As a result, computer 54 may automatically determine an occupant's music preference without affirmative interaction with the occupant. In addition, computer 54 may coordinate emotional responses to locations, situations, time of day, upcoming actions, and previous actions to improve suggestions for better music in the future.

In still yet another example, computer 54 may track an occupant's health over time when computer 54 knows the occupant's identity. In this example, an occupant's mood (determined through stress and other indicators), blood pressure, and circulation, among other health attributes, may be tracked over time and in response to use of various modes of operation or routines. In addition, computer 54 may determine that various patterns exist such as low energy each Friday morning. As a result, computer 54 may suggest various actions that the occupant may take outside the vehicle, inside the vehicle, modes of operation that may be performed by the vehicle and the vehicle seat, actions taken solely by the vehicle seat. Computer 54 may also notice certain biological responses of the occupant to various meetings, locations, weather, in-vehicle activities (e.g., firm braking, evasive maneuvers), out-of-vehicle activities (e.g., coming from the gym, coming from a long meeting, returning from a trip at the airport).

In some embodiments, the computer 54 may collect data from the sensors and/or portable devices over time and tag physiological conditions as they become known (e.g., restful state, sleepy state, active state, moderate stress state, etc.). Over time, computer 54 may perform normalization and/or averaging processing to establish baseline data for each condition. In an illustrative embodiment, sensor data from an external device may be normalized and transmitted to computer 54, where computer 54 may merge the normalized data together. In an illustrative embodiment, predetermined actions within a vehicle (e.g., seat adjustment, heating, cooling, etc.) may be tailored to modify an occupant's physiological state such that it approaches or approximates a baseline state (e.g., from moderately stressed state to relaxed state, from moderately fatigued state to moderately alert state, etc.).

In another example, computer 54 may obtain ECG signal 58 as shown in FIG. 20. In the illustrative example, ECG signal 58 is single channel ECG signal. Computer 54 then considers several features of the ECG signal 58 such as time domain features which include, for example, time intervals between elements P, Q, R, S, and T waves along with their amplitudes as shown in FIG. 20 and associates the obtained data with an occupant stored in memory of compute 54.

Computer 54 may also extract time domain features from ECG signal 58 such as post-transform features (such as wavelet coefficients and distances in the wavelet domain, autocorrelation coefficients, discrete cosine transform without detecting fiducial points P, Q, R, S, etc. In addition, discrete cosine transform obviates any need for delineating ECG cycles at all.

In another example, computer 54 may obtain a photoplethysmographic (PPG) pulse 59 as shown in FIG. 21. In the illustrative example, features may be extracted from a PPG pulse 59 and associates the obtained data with an occupant stored in memory of computer 54.

In another example, certain vehicle features may be enabled or disabled based on the identity of the occupant. As an example, the computer 54 may detect that an owner's son who is sixteen is driving the vehicle. The computer 54 may also detect that an occupant other than one of the parents is in the passenger seat. As a result, the computer 54 may not allow the vehicle to be started due to pre-programmed restrictions put in place by the owner.

An insight mode may be used by the occupant to determine trends and changes in health, comfort, and state of mind over time. In one example, the electronics system 16 may determine an initial tension level of the occupant each day as the occupant returns home after work. Over time, the computer 54 may show that the tension relief, mode, for example, has reduced a tension level of the occupant over time so that the occupant is more relaxed when the occupant arrives at home. The computer 54 may communicate this information to the occupant via an in-vehicle display, an application used on a smart phone, tablet, or mobile computing device, or via a web browser. As a result, the occupant is able to see the changes over time caused by the electronics system 16.

Electronics system 16 includes ECG sensor system 18, oximetry sensor system 20, and control system 22 as shown in FIG. 8. Electronics system 16 may also include another occupancy sensor system that is configured to sense when an occupant has entered and existed vehicle seat 10. In one example, the occupancy sensor system includes a pressure switch which is biased to an open position and is moved to a closed position when an occupant sits on the vehicle seat. The pressure switch may be coupled to an input 543 of computer 54 (see FIG. 15) to cause oximetry sensor system 20 to initiate and perform a calibration cycle. While a pressure switch is discussed, any other suitable alternative may be used.

As discussed previously, ECG sensor system 18 includes first and second ECG sensor 24, 26, ECG mat 28, and ECG unit 30 as shown in FIG. 8. In one illustrative example, first and second ECG receivers 24, 26 are Plessey EPIC™ Ultra High Impedance Sensors (PS25102). ECG receivers 24, 26 are capacitance based receivers. ECG mat 28 is a conductive mat or any other suitable alternative. ECG unit 30 includes, for example, a Plessey Control and Interface Box (PS25001A) and a driven right leg circuit coupled to the Control and Interface Box.

In another illustrative embodiment, ECG sensor 34 is coupled to a seat cushion 36 and positioned to lie below trim 38 which extends around seat cushion 36 as shown in FIG. 16. ECG sensor 34 is configured to provide means for detecting electrical signals in occupant 50 through trim 38, first, second, and Nth clothing layers 41, 42, and 43N as shown in FIG. 16. In one example, trim 38 is cloth trim. However trim 38 may also be leather trim or any other suitable material. In this example, first clothing layer 41 is a shirt made of cotton. Second clothing layer 42 is an undershirt made from cotton. Nth clothing layer 43N may be a dress coat made from wool or any other suitable alternative. Nth clothing layer 43N may be one layer or may be additional layers.

In another illustrative embodiment, oximetry sensors 31, 32 are coupled to a seat cushion 44 included in seat bottom 12 and arranged to lie below trim 46 and extend around seat cushion 44 as shown in FIG. 17. Oximetry sensors 31, 32 are configured to detect oxygen content in an occupant's blood through trim 46, first, second, and Nth clothing layers 51, 52, and 53N as shown in FIG. 17. In one example, trim 46 is cloth. First clothing layer 51 is a pair of pants made from denim. Second clothing layer 52 is a pair of underpants made from cotton. Nth clothing layer 53N may be a pocket included in the pair of pants or any other suitable alternative. Nth clothing layer 53N may be one layer or multiple layers.

In another example, electronics system 16 may further include a thermal sensor system. The thermal sensor system may be coupled to control system 22 and be configured to provide information relating to temperature and humidity distribution around an occupant, information relating to injured areas of an occupant, and information relating to temperature gradients around an occupant.

In the example where information relating to temperature and humidity distribution around the occupant is provided, personalized and automatic adjustments to heating and cooling of the occupant may be provided by computer 54 using the vehicle's HVAC system to target portions of the occupant for treatment. As a result of knowing specific hot and cold spots on the occupant's body, adjustments to heating and cooling of the occupant may occur in real time without occupant direction or control.

In the example where information relating to injured areas of the occupant is provided, increased blood flow to injured muscle areas may indicate to computer 54 the need for cooling in the area to minimize swelling, to decrease support in the are so that pressure is minimized on the damage area, or provide massage to promote increased blood flow to the area. In the example where information relating to temperature gradients around the occupant is provided, cooperation with other anthropometric data may be useful to target responses of the vehicle and vehicle seat.

The thermal sensor system may include a hydrothermal mat that includes heat-sensitive layers or an array of temperature sensors. The hydrothermal mat may be positioned to lie below the trim of the vehicle seat and be configured to sense heat through the trim whether the trim is cloth or leather. The hydrothermal mat would obtain heat information about a back side of the occupant. The thermal sensor system may also include an infrared camera coupled to the vehicle in such a position as to scan the occupant while seated in the vehicle seat. In another example, the infrared camera may be coupled to the vehicle in such a location so as to scan the occupant prior to being seated on the vehicle seat. An interface for providing such a scan and orienting the occupant during the scan may be the Faurecia SMARTFIT® technology.

Automobile sensor systems may be used to sense and monitor vehicle performance, including engine performance and diagnostics, tire pressure and security. Additional interest has developed in using other types of automobile sensor systems to monitor and enhance certain aspects of the end-user automobile driving experience. For example, automobile seat sensor technology has been deployed to enable such systems to identify automobile drivers, provide automobile security, enhance child safety, and the like.

With regard to automobile seat sensor systems, many systems provide limited information regarding (i) environmental and/or physiological parameters of occupants, and (ii) occupant seating environment and/or automobile cabin environment. Furthermore, certain sensors within such systems may be limiting, in that many sensors are cumbersome to integrate into the seating system, and awkward to deploy on the person of the occupant in the seat. For example, certain systems may require that sensors be physically attached to the skin of the occupant in order to detect physiological states or conditions. Other systems require occupants to wear custom-made clothing containing the sensors necessary for physiological detection. Moreover, the physiological datasets produced by conventional sensor systems do not adequately take into consideration the data produced from multiple, and sometimes different, types of sensors that may be part of a seat sensor system.

Accordingly, there is a need in to have a seat sensor system that is flexible to use and is capable of accommodating different kinds of occupants. The seat sensor system should be capable of detecting certain physiological parameters through one or more layers of clothing. The seat sensor system should also combine data produced from multiple sensors to provide more robust occupant physiological measurement.

Another seat sensor system 600 in accordance with the present disclosure is shown, for example, in FIG. 22. Seat sensor system 600 includes one or more galvanic skin response (GSR) sensors 601, one or more Pulse Ox sensors 602, discussed above, and particularly in connection with FIGS. 3, 6-7, 10, and 18, one or more ECG sensors 603 discussed above, and particularly in connection with FIGS. 1-2, 4-5, and 8, one or more temperature sensors 604, vehicle user interfaces 605, which may include one or more displays, seating controls 606, one or more occupancy sensors 607, and other sensors 608, which may include cameras and/or microphones, equipped with suitable audio/video processing capabilities. Items 601-608 are coupled to a processing apparatus 611, such as a computing device, which is equipped with sensor processing 612 and biometrics processing 613. While processing 612-613 is shown as two processors in FIG. 22, equivalent functions could be achieved using a single processor, or other multiples of processors.

Processing apparatus 611 is configured to communicate with one or more portable devices 609 and a remote processing and/or storage facility 610. A portable device 609 may include a cell phone, tablet, laptop, wearable processor (e.g., FuelBand™, FitBit™) or any other suitable device, and be further configured to communicate with facility 610. Facility 610 is configured to provide larger-scale storage for processing apparatus 611, and further provide additional processing capabilities that may be offloaded from processing apparatus 611.

A GSR sensor 601 may be used to obtain data related to body tissue conductance. Body tissue conductance sensors can potentially give you a wide array of information from electrodermal activity (EDA) to the level of hydration and the fat percentage of an occupant's body tissue. An illustrative GSR sensor 601 includes two electrodes 703, 704 placed on different portions of the body and a small current is passed between them to assess the resistance of the body's tissue.

As shown in FIG. 23, GSR sensor 601 is modeled using a chirp current electrode 703 in which an AC signal is input into a target which includes a dielectric 702 and a conductive medium 701. This signal is then detected by an EPIC sensor 704 after passing through dielectric 702 and conductive medium 701. The change in signal as evaluated through an RMS spectral density of the output signal provides insight about the materials through which the signal was passed.

In one illustrative example of use, GSR sensor 601 may be used to determine emotional responses of an occupant resting on a vehicle seat. Design of GSR sensor 601 models an occupant's skin as a resistor and the clothing as a capacitor in an RC circuit as suggested in FIGS. 24A-24C. By looking at the amplitude and phase shift created by this RC circuit, one can determine the specific values of the circuit and derive changes in the skin resistance similar to previous investigations using contact-based EDA sensors with A/C exciter currents. Changes in skin resistance may be correlated with various emotional states of an occupant.

ECG sensor(s) 603 are configured to provide an ECG signal 618 to sensor processing 612 as suggested in FIGS. 22 and 25. During sensor processing 612, ECG signal 618 is passed to operation 621 where ECG signal 618 is passed through a digital filter to provide a filtered signal 641. Depending on the use of ECG signal 618, various digital filters are applied. In one example, the digital filter a low pass digital filter with a cut-off of about 30 Hz and is applied to the ECG signal regardless of use. In another example, the digital filter is a band pass filter of about 0.1 Hz to about 0.25 Hz when used for determining respiration. In another example, the digital filter is a band pass filter of about 0.75 Hz to about 6 Hz when used for determining pulse. In still yet another example, the digital filter is a band pass filter of about 0.5 Hz to about 30 Hz when used for determining heart rate.

Filtered signal 641 then proceeds to operation 624 where peak cleaning and reliability of the signal is determined as suggested in FIG. 25 and shown in FIG. 26. From there, the ECG signal may be used to determine biometric data such as a best ECG signal 627 and heart rate variability 628 and combined with pulse ox signal(s) 619 to provide an average heart rate 629, pulse arrival time 630, respiration 631, a best pulse ox signal 632 as shown in FIG. 25.

During operation 624, several sub-operations occur. As shown in FIG. 26, filtered signal 641 is buffered to provide a portion of filtered signal during operation 642. In one example, the portion of filtered signal 641 is about 100 milliseconds to about 1,000 milliseconds of sensor data. Operation 624 then proceeds to sub-operation 643 in which peaks in the buffered filtered signal are detected. In one example, the threshold for peak detection is set based on a height of the last detected peak multiplied by a time dependent decay. This allows the threshold to automatically adjust to a wide range of signal amplitudes. The leak decay multiplier may be set at about 0.5/second so that after one second of no detected peaks, the amplitude is half the last peak.

Next, operation 624 proceeds to sub-operation 644 in which Inter-Beat Intervals (IBI) are calculated using the peaks detected in sub-operation 643. In one example, IBI is the time elapsed between two consecutive detected peaks. In another example, some peaks may be either undetected (in which case the IBI would be too large) or noise artifacts (in which case the IBI would be too short). As a result, further processing is needed to obtain the desired IBI's.

Operation 624 then proceeds to a sub-operation 645 in which short IBI's are removed so as to remove noise artifacts. In one example, IBI's that are less about 300 milliseconds are removed. Once the short IBI's are removed, operation 624 proceeds to a sub-operation 646 in which the last several IBI's are buffered to provide a data set distribution of IBI's which is evaluated during sub-operation 653 as shown in FIG. 26.

During sub-operation 653, the data set distribution of buffered IBI's is evaluated by calculating various statistics related to the data set. Sub-operation 653 includes several operations which include a delta reliability operation 647 in which a calculation is performed to determine how much the current IBI deviates from the median IBI (denoted as delta reliability). Sub-operation 653 further includes a distribution reliability operation 649 in which a calculation is performed to determine the Median Absolute Deviation (MAD) of the data set distribution. In one example, 1.5 multiplied by the MAD is used as a proxy for standard deviation of the data set distribution. Once delta reliability and the MAD are determined, sigmoid transfer function operations 648, 650 are applied using the inputs of delta reliability and (1.5*MAD). The lower the delta reliability (normalized by the standard deviation), the higher the reliability and vise versa, with the reliability falls off sharply after a certain threshold (depending on the parameters of the sigmoid function).

Once the operations 648, 650 are complete, sup-operation proceeds to a geometric average operation 651 in which a calculation of a ratio of MAD of IBI distribution to MAD of a uniform distribution on the range of +/−80*log(n) around the median of IBI distribution (where n is the size of the IBI buffer). This measure is used to assess the general non-uniformity of the IBI distribution, with the idea that the more uniform and wider the distribution, the less it is trustworthy. The ratio is identified for future use as H. The reliability of the distribution is then linearly decreasing with this measure: 1−min(H,1). The total reliability of the peak/IBI is calculated as a geometric average of the delta reliability and the distribution reliability, namely, sqrt(r(delta)*r(distribution)). Those IBI for which the total reliability is above a certain threshold (50% by default) are retained for the HRV spectrum calculation. A reliability score 652 is then output.

Pulse Ox sensors 602 are configured to provide a Pulse Ox signal(s) 619 to sensor processing 612 as suggested in FIGS. 22 and 25. During sensor processing 612, Pulse Ox signal(s) 619 is passed to operations 622, 623 where Pulse Ox signal(s) 619 are passed through associated digital filters. When determining ECG, digital filters are band pass filters of about 8 Hz to about 20 Hz.

Depending on which biological data is being determined from the Pulse Ox signal 619, sensor processing 612 may handle Pulse Ox signal 619 differently. In the example of where Pulse Ox signal 619 is used to determine average heart rate 629, pulse transit time 630, respiration 631, and pulse ox best 632, filtered signal 641 goes through a similar set of operations 642-651 to provide a reliability of filtered signal 641. In the example where Pulse Ox signal 619 is used to determine respiration 631, Pulse Ox signal 619 is passed through operation 626 in which peaks and valleys are both detected.

Once sensor processing 612 is complete, the signals are then provided for biometric processing 613 in which biological data is calculated. In a first example, an ECG signal from each ECG receiver 24, 26 is then used to calculate Heart Rate (HR). HR is calculated as 60 seconds divided by IBI. In one example, each ECG receiver 24, 26 is used to calculate an associated HR 654-657 as shown in FIG. 27. HR 654 from first ECG receiver 24 is provided to a time-dependent weighting operation 655 followed by reliability score dependent weighting operation 656. HR 657 from second ECG receiver 26 is provided to a similar time-dependent weighting operation 658 followed by a similar reliability score dependent weighting operation 659. Together all the operations 655, 656, 658, 659 are then used in a reliability score weighted grand average 660 so that an average heart rate reliability 661 is provided.

During time-dependent weighting operations 655, 658, a decay of each HR 654, 657 is determined. The concept being that the older the HR, the less relevant it should be for the current calculation. The decay may be an exponential of the time difference between the time of the HR and now (the time of the calculation), scaled by an appropriate constant as shown in the formula below:

$$decay_i = \exp(-(timeNow - time_i)/scale)$$

Average HR is then the weighted average of the HR signal with weights given by decay multiplied by reliability. Reliability may be calculated in a similar manner as discussed previously with operations 642-651:

$$\frac{\sum_i HR_i \times reliability_i \times decay_i}{\sum_i reliability_i \times decay_i}$$

The average reliability is the weighted average of the reliabilities with weights given by decay. In addition, reliability may be punished by the time passed between the last signal and now because we want reliability to fall when the signal becomes stale. Therefore, the weighted average is multiplied by the last decay:

$$\frac{\sum_i reliability_i \times decay_i}{\sum_i decay_i} \times decay_N$$

In another example, Heart Rate Variability (HRV) 628 along with reliability of HRV may be determined as shown in FIG. 28. To begin calculated HRV, IBI for ECG and Pulse Ox along with associated time stamps and reliability scores are used to calculate HRV spectrum 668 and LF/HF score 669. The process begins with a reliability score threshold operation 662 in which only those IBI's with a sufficient reliability score, for example, about 0.5, are used. The process then proceeds to a buffering operation 663 in which the reliable IBI's are accumulated for a period of time, for example, greater than about one minute in order to achieve sufficiently low frequency estimates for low frequency calculation. The process then proceeds to a resample operation 664 in which the timestamps of each IBI and the IBI buffer are then spline resampled to a fixed sampling rate. The process then proceeds to a spectral analysis 665 operation in which spectral analysis is performed on the resampled time series and HRV spectrum 668 is output. The process then proceeds to a calculate frequencies operation 666 in which the LF/(HF+LF) ratio is calculated. The process may then proceed to an optional smoothing operation 667 in which the LF/(HF+LF) ration is smoothed to reduce noise. The LF/HF score 669 is then output.

In another example, Pulse Arrival Time (PAT) 630, also called Pulse Transit Time (PTT) 630, is calculated along with blood pressure 634 as shown in FIG. 29. PTT is the time elapsed between a heartbeat observed in the ECG signal and the corresponding heartbeat observed in the Pulse Ox signal. These values are calculated beginning with inputs of ECG peaks and associated reliability scores 671 and pulse ox peaks and associated reliability scores 672 to a PAT calculation operation 673 as shown in FIG. 29. PAT calculation operation 673 begins with assuming a minimal PTT of about 150 milliseconds. Maximum PTT is calculated as the IBI implied by the current average heart rate plus minimum PTT. For each Pulse Ox heart beat at time t, the closest prior ECG heart beat in the interval [t-max PTT, t-min PTT]. If no such heart beat is identified, the operation 673 proceeds to the next Pulse Ox heartbeat, otherwise, PTT is calculated as the time difference of the beats, with reliability equal to the product of corresponding beat reliabilities. The process then proceeds to a weighted smoothing operation 676 in which average PTT is calculated by weighted average of smoothed PTT's of both pulse ox sensor signals.

Blood pressure 634 is then calculated during blood pressure calculation operation 677 as shown in FIG. 29. Using PTT 630, systolic and diastolic blood pressure using linear estimations algorithms. In one example, diastolic blood pressure (DBP) is estimated at 75−0.01*PTT. Systolic blood pressure (SBP) is estimated as 200−(0.3*PTT).

Accuracy of blood pressure 634 may be increased through calibration of seat sensor system 600 to a known blood pressure value for an occupant. In one example, an occupant has their blood pressure obtained using a blood pressure cuff and then enters the data into seat sensor system 600. In another example, an electronic blood pressure cuff is coupled to an occupant while the occupant is resting on a vehicle seat including seat sensor system 600. The electronic blood pressure cuff them communicates with seat sensor system 600 to calibrate seat sensor system 600 while seat sensor system 600 is calculating blood pressure from pulse transit time so that the determined pulse transit time is calibrated to a known blood pressure reading in real time.

Seat sensor system 600 includes a communication module for communicating with other devices (e.g., smart phones, tablets, computers, activity trackers, medical devices), networks (e.g., the internet, a private network, the cloud), and other modules included in the vehicle. Such a communication module may be included in the vehicle seat, included in the vehicle and part of the vehicle equipment separate from the vehicle seat, or any other suitable alternative.

In one example, the communication module allows seat sensor system 600 to communicate health information or any other biological data to an occupant's physician. In another example, the communication module allows seat sensor system 600 to communicate an occupant's mood to friends and family via a social application.

In a further example, seat sensor system 600 may receive information from other seat sensor systems 600 included in other vehicles. This crowdsourcing of data may allow other occupant's experiences and to suggest routines and modes of operation for the occupant. The crowdsourcing data may also suggest that other occupants are experiencing increased stress due to problems with their travel route causing seat sensor system 600 to suggest an alternate route and/or modes of operation which minimize such increase in stress or tension.

Data may also come from other occupants riding within the vehicle to provide feedback to the driver occupant. In one illustrative example, a seat sensor system included in a passenger seat may determine that a chauffeur's driving style is scaring the passenger. As a result, seat sensor system 600 may suggest ways to alter the driving style to minimize the passenger's fear and anxiety.

Another embodiment of a vehicle seat 810, in accordance with the present disclosure, includes a seat bottom 12, a seat back 14, and an electronics system 816 as shown FIG. 30. Electronics system 816 is configured to sense one or more physiological attributes of an occupant (not shown) sitting on vehicle seat 810 through clothing worn by the occupant, so that a predetermined action may be taken in response to the physiological attribute detected by electronics system 816. In one illustrative example, the predetermined action may be audio, visual, or tactile feedback provided by vehicle seat 10 to the occupant.

As shown in FIG. 30, electronics system 816 comprises an electrocardiogram (ECG) sensor system 818, an oximetry sensor system 820, and a control system 822. ECG sensor system 818 is coupled to seat back 14 to sense electrical signals provided by the occupant. Oximetry sensor system 820 is coupled to seat bottom 12 to sense oxygen content in the occupant's blood. Control system 822 is coupled to the ECG sensor system 18 and oximetry sensor system 20 to receive signals provided by each system, process the signals, make calculations using the signals, and determine physiological attributes of the occupant. Control system 822 may perform one or more predetermined actions based on the physiological attributes of the occupant.

ECG sensor system 818 includes, for example, a first ECG receiver 24, a second ECG receiver 26, a third ECG receiver 25, a fourth ECG receiver 27, an ECG Drive Right Leg (DRL) unit 828, and an ECG unit 30 as suggested in FIG. 30. First, second, third, and fourth ECG receivers 24, 25, 26, 27 are coupled to seat back 14 to lie in spaced-apart relation to one another and lie in spaced-apart relation above seat bottom 12. ECG DRL 828 in one example is coupled to seat bottom 12 and lie under the thighs of an occupant 50. In another example ECG DRL 828 is included in a steering wheel, a gear selector, gear shifter, and/or any other suitable locations included in the vehicle or vehicle seat.

In one example, ECG receivers 24, 25, 26, 27 are use two at a time and may be aligned as suggested in FIG. 1. In one example, ECG receivers 24 and 27 are selected to be used to sense electrical signals provided by the occupant's body. In another example, other combinations of ECG receivers 24, 25, 26, 27 may be used to sense electrical signals from the occupant's body. The combination of ECG receivers 24, 25, 26, 27 may be selected by the occupant based on size and shape of the occupant's body. The combination of ECG receivers 24, 25, 26, 27 may also be selected automatically by computer 54 according to the most reliable ECG receivers 24, 25, 26, 27. The sensed electrical signals are then transformed by a driven right leg circuit included in ECG unit 30 and passed through ECG DRL 828 which may be located at any suitable location in vehicle seat 810 or the vehicle. ECG DRL 828 then sends the signals back through occupant 50 where the signals are detected again by two of ECG receivers 24, 25, 26, 27 passed through ECG unit 30 and sent to control system 822. As a result, ECG sensor system 818 minimizes noise so that the remaining signal is associated more closely with an occupant's heart rate.

ECG receivers 24, 25, 26, 27 and ECG DRL 828 cooperate to provide an ECG sensor. ECG sensor is coupled to a seat cushion 36 and surrounded by trim 837, which may be cloth or leather, as shown in FIG. 1. ECG sensor is configured to provide means for detecting electrical signals in occupant 50 through first, second, and $N^{th}$ clothing layers 41, 42, and 43N as suggested in FIG. 2. In one example, first clothing layer 41 is a shirt made of cotton. Second clothing layer 42 is an undershirt made from cotton. Nth clothing layer 43N may be yet another undershirt made from polyester. $N^{th}$ clothing layer 43N may be one layer or may be additional layers.

In one example, trim 837 is perforated leather. Perforated leather is leather trim in which a plurality of small holes are formed in the leather so as to maximize ventilation of air between the occupant's skin and the leather. In another example, the various holes may be filled with material which has a higher conductivity than leather such a synthetic leather, a synthetic leather impregnated with conductive particles, an elastomeric material, an elastomeric material impregnated with conductive materials, or any other suitable alternative.

Oximetry sensor system 820 includes a first oximetry sensor 831 and a second oximetry sensor 832 as shown in FIG. 1. Oximetry sensors 831, 832 are coupled to seat bottom 12 as shown in FIG. 1. Oximetry sensors 831, 832 are spaced apart from one another and aligned with one another to both sense the same leg of the occupant. Each oximetry sensor 831, 832 is arranged to sense oxygen content in the occupant's blood. Each oximetry sensor 831, 832 emits light at a wavelength which passes through clothing layers 41, 42, 43N and enters occupant's skin 40 where a portion of the light is absorbed by the occupant's blood. The remaining portion of the light is reflected by the occupant's blood back through clothing layers 41, 42, 43N and is detected by each oximetry sensor 831, 832. The detected light is converted to an oximetry signal and sent to control system 822.

As a result of both oximetry sensors 831, 832 being located along the same leg of an occupant, determination of pulse arrival time 630 and blood pressure 634 may be simplified. As discussed previously, pulse arrival time 630 is the time elapsed between a heartbeat observed by first oximetry sensor 831 and the corresponding heartbeat observed by the second oximetry sensor 832. These values are calculated beginning with inputs pulse ox peaks and associated reliability scores for both pulse ox sensors 831, 832. Distance between pulse ox sensors 831, 832 is known and fixed, thus a time between detected peaks provides for a velocity of blood flowing in the area of the occupant's leg and PTT. Blood pressure 634 is related to the velocity of blood flow in that higher velocity indicates higher blood pressure and lower velocity indicates lower blood pressure. In one example, diastolic blood pressure (DBP) is estimated as 75−0.01*PTT and systolic blood pressure (SBP) is estimated as 200−(0.3*PTT).

Both oximetry sensors 831, 832 may be arranged along the right leg of an occupant. The right leg may be chosen as the driver of the vehicle uses the right leg to control the accelerator of the vehicle. As a result, contact with oximetry sensors 831, 832 is maintained and maximized.

As shown in FIG. 1, each oximetry sensor 31, 32 is configured to communicate light to and from the occupant through apertures 833, 835 associated with each oximetry sensor 31, 32. In on example, apertures 833, 835 are formed in trim 837. Trim 837 may be cloth, leather, or any other suitable material.

In an illustrative embodiment, a ballistocardiogram (BCG) sensor may also be embedded in a portion of vehicle seat 810, such as a backrest portion 839 to sense BCG data from an occupant and produce BCG signal 838. The BCG data and resultant signal 838 may comprise data relating to ballistic forces on the heart, and a BCG curve may be generated as a graphical representation of repetitive motions of the occupant's body arising from the sudden ejection of blood into the vessels with each heart beat. In an illustrative embodiment, the BCG sensor may comprise electromechanical film (EMFi) sensors such as a piezoelectric sensor or sensor pad embedded into seat portion 839 which transfer mechanical energy to electrical signal and vice versa.

In an illustrative embodiment, an accelerometer arrangement may be provided as part of BCG sensor 839 to sense acceleration BCG, which may be monitored by two MEMS accelerometers placed behind the BCG sensor. The accelerometers may be positioned towards a bottom portion of the BCG sensor 839 to minimize the effects of cervical and thoracic movements, and to ensure proximity to the trunk support, thus mitigating the effects of leg movement or lateral leaning. The accelerometer may output analog voltages representing each axis' acceleration with a sensitivity of 1 V/G. Such a configuration may be used to compensate for artifacts in the BCG sensing, and may also be used to detect the user's transfer from or into the seat 810.

In another illustrative embodiment, the BCG sensor may comprise optical sensors, where an optical interferometer may be configured to obtain signal that includes information about the heart activity. In another illustrative embodiment, the BCG signal 838 can be measured by radar system waves on very high frequencies as well.

The heart rate from the BCG signal can be detected by various techniques, such as signal segmentation with template beat wave model matching. Another illustrative technique comprises the use of adaptive beat to beat estimation based on component analyses. Neural network algorithms on a FPGA may also be used to detect heart beats from BCG. As BCG sensing may sometimes experience movement artifacts from the occupant, digital signal processing may be used, such as adaptive filters, fusion of complementary information by accelerometry or electromyography, as well as wavelet analysis, and empirical mode decomposition, to reduce such artifacts.

The terms algorithm or module as used herein do not limit the functionality to particular physical modules, but may include any number of tangible software and/or hardware components. In general, a computer program product in accordance with one embodiment comprises a tangible computer usable medium (e.g., standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Objective-C, Javascript, CSS, XML, etc.).

An exemplary vehicle system 3101 comprising various vehicle electronics subsystems and/or components including any of the sensor configurations discussed above is shown in FIG. 31. Engine/transmission module 3102 is configured to process and provide vehicle engine and transmission characteristic or parameter data, and may comprise an engine control unit (ECU), and a transmission control. Global positioning system (GPS) module 3103 provides location data for vehicle 3101. Sensors 1104 provides sensor data which may comprise data relating to any of the seat sensors described above, and may also comprise data relating to any vehicle characteristic and/or parameter data (e.g., from 3102), and may also provide environmental data pertaining to the vehicle, its interior and/or surroundings, such as temperature, humidity and the like. Sensors 1104 may further include collision detection sensors that may sense a vehicle collision. The vehicle system 3101 may be configured to transmit data from seat sensors in 1104 in conjunction with certain detections made from vehicle sensors 1104. For example, vehicle system 3101 may be configured to transmit automatically (e.g., via 3106) past and/or present physiological data from seat sensors 1104 upon the detection of a collision.

Radio/entertainment module 105 may provide data relating to audio/video media being played in vehicle 3101. Module 3105 may be integrated and/or communicatively coupled to an entertainment unit configured to play AM/FM radio, satellite radio, compact disks, DVDs, digital media, streaming media and the like. Communications module 3106 allows any of the modules in FIG. 31 to communicate with each other and/or external devices via a wired connection or wireless protocol, such as Wi-Fi, Bluetooth, NFC, etc. In one embodiment, modules 3102-3106 may be communicatively coupled to bus 3112 for certain communication and data exchange purposes.

Vehicle 3101 may further comprise a main processor 3107 that centrally processes and controls data communication throughout the system of FIG. 1. Main processor may be embodied as computer 54 discussed above, or may be part of a processing system that includes computer 54 that provides and/or assists in performing any of the functions described herein. Storage 3108 may be configured to store data from any device and/or component of vehicle system 3101 including, but not limited to, software, sensor data, sensor processing algorithms, media, files and the like. Digital signal processor (DSP) 3109 may comprise a processor separate from main processor 3107, or may be integrated within processor 3107. Generally speaking, DSP 3109 may be configured to take signals, such as sensor signals, voice, audio, video, temperature, pressure, position, etc. that have been digitized and then mathematically manipulate them as needed. Display 3110 may be configured to provide visual (as well as audio) indicial from any module in FIG. 31, and may be a configured as a LCD, LED, OLED, or any other suitable display. Display may also be configured with audio speakers for providing audio output. Input/output module 3111 is configured to provide data input via key pads, touch screens, joystick controllers and the like, and outputs to/from other peripheral devices. Users (occupants) may manually enter data, such as user profile data and/or control signals for setting and/or responding to sensors. As discussed above, modules 3107-3111 may be communicatively coupled to data bus 3112 for transmitting/receiving data and information from other modules.

An exemplary embodiment is illustrated, where a vehicle 3101 (see FIG. 31), is paired with one or more devices 3201 (3202, 3203) which may be registered to one or more users (occupants) as shown in FIG. 32. Devices 3201 may comprise smart phones, health/fitness monitoring devices, tablets, laptops, and the like. In some embodiments, devices 3201 may be registered with vehicle 101 using Bluetooth pairing or using WiFi or NFC registration, as is known in the art. In some illustrative embodiments, device 3201 registrations are stored (e.g., 3108) at the vehicle according to a device ID or SIM ID, and may further include a device user profile (occupant profile data) associated with each ID that may include demographic data, health data, including age, gender, weight, previous sensor reading data, user interests, and/or user sensor/device/vehicle history. Devices 3202, 3203 are configured to receive vehicle/seat characteristic and/or parameter from vehicle 3101, and are further configured to communicate with each other as shown in FIG. 32. Portable devices 3201 are also configured to communicate with wireless network 3204 in order to send/receive data from a central server 3205. In one embodiment, vehicle 3101 may also be configured to communicate with network 3204. Server 3205 may be also configured to perform back-end processing for devices 3201 and vehicle 3101, and further communicate with other remote servers for additional functionalities, such as software application, media servers, social media, and the like.

In some illustrative embodiments, sensor data and/or processed data from any of the sensors may be transmitted from vehicle 3101 to server 3205, which may be a stand-alone server, or part of a server group or cloud. Server 3205 may also collect data including sensor data and/or processed sensor from other vehicles similarly equipped as vehicle 3101. In one embodiment, server 3205 receives raw sensor data and performs any of the techniques described above to determine physiological attributes of users (i.e., occupants of a plurality of vehicles). In another embodiment, server 3205 receives processed sensor data that indicates a physiological attribute. Server 3205 may be further configured to process other vehicle sensor data (e.g., speed, acceleration, braking, etc.) and other vehicle characteristic data (e.g., seating position, activation of entertainment system, etc.) and location data (e.g., GPS coordinates) and combine such data to create vehicle and/or location profiles for use in seating feature adjustment.

For example, server 3205 may receive sensor data for multiple vehicles at a particular location and determine that users experience high stress in that location, which may be attributable to traffic congestion, poor road design, and the like. Determining that stress levels are generally high for the area, server 3205 may transmit control signals and/or algorithms to vehicles to activate or deactivate seat features (e.g., massage, heating/cooling), adjust seat positioning parameters, and/or activate other vehicle features (e.g., activate soothing music playlist on entertainment system) when vehicles approach the vicinity of the location. Server 3205 may process user profile data with the sensor data to make further determinations. For example, server 3205 may determine that users/occupants of a particular height, weight, age, etc. experience stress in a particular location. Accordingly, server 3205 may transmit control signals and/or algorithms to vehicles having occupants meeting the height, weight, age, etc. profile to activate or deactivate seat features, adjust seat positioning parameters, and/or activate other vehicle features when vehicles approach the vicinity of the location. Server 3205 may also make observations over time regarding one or more user physiological states as they relate to a vehicle use characteristic, and proactively provide adjustments via control signals and/or algorithms to the vehicle. For example, server 3205 may determine over time that a user is in a relaxed state when a seat is slightly declined from a normal seat position during slower driving speeds and experiences reduced stress when the seat is inclined slightly during faster driving speeds. By learning a user's physiological states under various driving/vehicle conditions, server 3205 may provide further improved adjustments to a user's seat and/or vehicle's features to better the user's driving experience.

Of course, certain features of server 3205 may be contained within computer 54 that may comprise processor 3107. Also, certain features of server may be performed by devices 3201. In one illustrative embodiment, computer 54 may batch sensor data and transmit it to a device (e.g., device 3202) for storage at predetermined times. The device may subsequently process the sensor data, or interact with server 3205, and provide feedback to a user via a software program or app regarding physiological states and their relationship to vehicle usage and/or vehicle locations. By providing a user interface with such software, users may manually adjust and customize actions performed for particular physiological events. In an illustrative embodiment, the device (e.g., device 3202) may be configured to generate an automated emergency call, and/or transmit the physiological condition data if physiological characteristics are outside predetermined parameters (e.g., attack alert). The vehicle communications 3106 may also be configured to provide these features as well.

The following numbered clauses include embodiments that are contemplated and non-limiting:

Clause 1. An occupant support system comprising an electronics system for a vehicle seat, the electronics system comprising a sensor system configured to obtain sensor data from an occupant of the seat, wherein the sensor system is configured to obtain at least a portion of the sensor data from the occupant through at least one impeding barrier, the sensor data comprising occupant data associated with the occupant of the seat and a computer coupled to the sensor system, the computer comprising processing means for processing the sensor data including occupant data received from the occupant and configured to perform a predetermined action using the occupant data.

Clause 2. A vehicle system, comprising a vehicle sensor system for producing vehicle usage characteristic data;

an electronics system for a vehicle seat comprising a sensor system configured to obtain sensor data from an occupant of the seat, wherein the sensor system is configured to obtain at least a portion of the sensor data from the occupant through at least one impeding barrier, the sensor data comprising occupant data associated with the occupant of the seat and a computer coupled to the sensor system and the vehicle sensor system, the computer comprising a processor to (i) process the sensor data to determine a physiological state of the occupant, and (ii) process the vehicle usage characteristic data to determine a vehicle usage characteristic, the computer being configured to generate one or more control signals to perform a predetermined action associated with the physiological state and vehicle usage characteristic.

Clause 3. The occupant support system of any other clause, wherein the sensor system comprises a sensor coupled to the vehicle seat, configured to sense a physiological attribute of the occupant, and configured to provide at least a portion of the occupant data using the physiological attribute.

Clause 4. The occupant support system of any other clause, wherein the sensor is located between a cushion of the seat and a trim layer of the seat, the sensor is further configured to sense the physiological attribute through the at least one impeding barrier comprising at least one of the trim layer and occupant's clothing and the trim layer.

Clause 5. The occupant support system of any other clause, wherein the sensor is one of an electrocardiogram (ECG) sensor, a pulse oxymetry sensor, and a galvanic skin response sensor.

Clause 6. The occupant support system of any other clause, wherein the sensor comprises a ballistocardiogram (BCG) sensor.

Clause 7. The occupant support system of any other clause, wherein the sensor system comprises a first sensor coupled to the seat in a first location and configured to provide a first sensor signal and a second sensor coupled to the seat in spaced-apart relation to the first sensor to provide a second sensor signal, the first and second sensors cooperate to sense at least one physiological attribute of the occupant through the at least one impeding barrier, and the first and second sensors are configured to communicate to the computer the first and second sensor signals.

Clause 8. The occupant support system of any other clause, wherein the computer is further configured to determine a reliability associated with each sensor signal, compare reliability of each sensor signal, and use one or more sensor signals having reliability greater than a predetermined value to provide at least the portion of the occupant data.

Clause 9. The occupant support system of any other clause, wherein the computer is further configured to compare the first and second sensor signals to provide derivative information included in the occupant data.

Clause 10. The occupant support system of any other clause, wherein the computer is further configured to determine a blood pressure of the occupant using the derivative information.

Clause 11. The occupant support system of any other clause, wherein the derivative information comprises a pulse transit time.

Clause 12. The occupant support system of any other clause, wherein the sensor system comprises a first sensor coupled to the seat in a fixed position relative to the seat to sense a physiological attribute of the occupant through the at least one impeding barrier to provide a first sensor signal associated with the physiological attribute.

Clause 13. The occupant support system of any other clause, wherein the computer is further configured to receive occupant profile data associated with the occupant and combine the occupant profile data with the occupant data, and performing the predetermined action using the occupant data and the occupant profile data.

Clause 14. The occupant support system of any other clause, wherein the computer is configured to perform the predetermined action by determining an identity of the occupant using at least one of the occupant data and the occupant profile data.

Clause 15. The occupant support system of any other clause, wherein the at least one of the occupant data and the occupant profile data comprises an electrocardiogram (ECG) wave form.

Clause 16. The occupant support system of any other clause, wherein the computer is configured to perform the predetermined action by determining a driver capability assessment using at least one of the occupant data and the occupant profile data.

Clause 17. The occupant support system of any other clause, wherein the computer is configured to determine the driver capability assessment by analyzing respiration rate and processing rate changes over time.

Clause 18. The occupant support system of any other clause, wherein the computer is configured to perform the predetermined action by determining a driver stress level using at least one of the occupant data and the occupant profile data.

Clause 19. The occupant support system of any other clause, wherein the computer is configured to determine the driver stress level by analyzing heart rate variability.

Clause 20. The occupant support system of any other clause, wherein the computer is configured to perform the predetermined action by determining a health metric using at least one of the occupant data and the occupant profile data.

Clause 21. The occupant support system of any other clause, wherein the computer is configured to determine the health metric by calculating at least one of blood pressure, resting heart rate, and recovery time, the computer being further configured to receive factors including at least age, gender, weight, and combine the at least one of blood pressure, resting heart rate, and recovery time with factors to determine the health metric.

Clause 22. The occupant support system of any other clause, wherein the computer is configured to perform the predetermined action by determining a blood-flow metric using at least one of the occupant data and the outside occupant data.

Clause 23. The occupant support system of any other clause, wherein the computer is configured to determine the blood-flow metric by calculating blood volume data.

Clause 24. The occupant support system of any other clause, wherein the computer is further configured to receive occupant profile data associated with the occupant, and to determine a baseline state associate with the occupant using the outside occupant data.

Clause 25. The occupant support system of any other clause, wherein the computer is further configured to determine a current state of the occupant using the occupant data, compare the current state with the baseline state, and perform the predetermined action using the comparison of the current state and the baseline state.

Clause 26. The occupant support system of any other clause, wherein the computer is further configured to perform the predetermined action by adjusting occupant comfort via adjusting the seat to cause at least some of current state parameters to approximate at least some of baseline state parameters.

Clause 27. The occupant support system of any other clause, wherein the computer is further configured to perform the predetermined action by adjusting thermal comfort of the occupant by adjusting a thermal device in the seat to cause at least some of current state parameters to approximate at least some of baseline state parameters.

Clause 28. The occupant support system of any other clause, wherein the computer is further configured to perform the predetermined action by reducing stress parameters of the occupant by performing at least one of engaging a massage system coupled to the seat, adjusting an arrangement of the seat, and engaging a thermal device in the seat to cause at least some of current state parameters to approximate at least some of baseline state parameters.

Clause 29. The occupant support system of any other clause, wherein the computer is further configured to perform the predetermined action by increasing energy parameters of the occupant by performing at least one of engaging a massage system coupled to the seat, adjusting the seat to assume an upright arrangement, and engaging a thermal device included in the seat to adjust a seat temperature for the occupant.

Clause 30. The occupant support system of any other clause, wherein the computer is further configured to perform the predetermined action by determining a driver stress level by analyzing heart rate variability using occupant data.

Clause 31. The occupant support system of any other clause, wherein the electronics system further includes a communication unit configured to transmit the driver stress level to a remote computer.

Clause 32. The occupant support system of any other clause, wherein the sensor system further includes a location sensor configured to provide location data indicative of a location of the occupant and the computer is further configured to receive the location data and merge the location data with the occupant data to cause a location-related stress level of the occupant to be determined.

Clause 33. The occupant support system of any other clause, wherein the computer is further configured to determine physiological conditions of the occupant using the occupant data and determining if at least one of the physiological conditions is below a predetermined value.

Clause 34. The occupant support system of any other clause, wherein the electronics system further includes a communication unit coupled to the computer to receive commands from the computer and configured to communicate the physiological conditions when the computer determines at least one physiological condition is below the predetermined value.

Clause 35. The occupant support system of any other clause, wherein the computer is further configured to determine physiological conditions of the occupant using the occupant data and store the physiological conditions over time to establish a collection of stored physiological conditions.

Clause 36. The occupant support system of any other clause, wherein the electronics system further includes a communication unit coupled to the computer to receive commands from the computer and configured to communicate the collection of stored physiological conditions to a remote computer.

Clause 37. The occupant support system of any other clause, wherein the physiological conditions includes blood pressure and wherein the computer is further configured to calculate a trend over time of physiological conditions and determine if the trend of vital signs exceeds a predetermined threshold.

Clause 38. The occupant support system of any other clause, wherein the electronics system further includes a communication unit coupled to the computer to receive commands from the computer and configured to communicate the collection of physiological conditions to a remote computer when the computer determines the trend of physiological conditions exceeds a predetermined threshold.

Clause 39. The occupant support system of any other clause, wherein the computer is further configured to receive occupant profile data, and wherein the computer processes and stores the sensor data over time and associates it with the profile data Clause 40. The occupant support system of any other clause, wherein the computer is configured to perform a different predetermined action using the processed and stored sensor data over time.

Clause 41. The occupant support system of any other clause, wherein the computer is further configured to perform the different predetermined action by adjusting occupant comfort via adjusting the seat to cause at least some of current state parameters of the sensor data over time to approximate at least some of baseline state parameters.

Clause 42. The occupant support system of any other clause, wherein the computer is further configured to perform the different predetermined action by adjusting thermal comfort of the occupant by adjusting a thermal device in the seat to cause at least some of current state parameters of the sensor data over time to approximate at least some of baseline state parameters.

Clause 43. The occupant support system of any other clause, wherein the computer is further configured to perform the different predetermined action by reducing stress parameters of the occupant by performing at least one of engaging a massage system coupled to the seat, adjusting an arrangement of the seat, and engaging a thermal device in the seat to cause at least some of current state parameters of the sensor data over time to approximate at least some of baseline state parameters.

Clause 44. The occupant support system of any other clause, wherein the computer is further configured to perform the different predetermined action by increasing energy parameters of the occupant by performing at least one of engaging a massage system coupled to the seat, adjusting the seat to assume an upright arrangement, and engaging a thermal device included in the seat to adjust a seat temperature for the occupant.

Clause 45. The occupant support system of any other clause, further comprising one or more vehicle sensors coupled to the computer for producing one or more vehicle usage characteristic data, and wherein the computer is configured to process the sensor data including occupant data and vehicle usage characteristic data to perform the predetermined action.

Clause 46. The occupant support system of any other clause, further comprising a communications device, coupled to the computer, wherein the computer is configured to transmit the occupant data via the communications device when the processed vehicle usage characteristic determines a vehicle event has occurred.

Clause 47. The vehicle system of any other clause, wherein the predetermined action comprises at least one of (1) modifying a physical configuration of the vehicle seat, (2) transmitting a message for presentation on a vehicle display, (3) transmitting a message for presentation on a vehicle speaker, (4) modifying a temperature of the vehicle seat, (5) activating a massaging device in the vehicle seat, (6) deactivating a massaging device in the vehicle seat, (7) transmitting the sensor data via a communication device in the vehicle system, (8) transmitting the physiological state via the communication device in the vehicle system, (9) transmitting the vehicle characteristic data via the communication device in the vehicle system, and (10) transmitting the vehicle characteristic via the communication device in the vehicle system.

Clause 48. The occupant support system of any other clause, wherein the computer is further configured to calculate at least one of heart rate and respiration rate of the occupant using the occupant data before performing the predetermined action.

Clause 49. The occupant support system of any other clause, wherein the first and second sensors are coupled to the seat bottom of the vehicle seat and arranged to underlie a right let of the occupant.

The invention claimed is:

1. An occupant support system comprising an electronics system for a vehicle seat, the electronics system comprising
a sensor system configured to obtain sensor data from an occupant of the seat, wherein the sensor system is configured to obtain at least a portion of the sensor data from the occupant through at least one impeding barrier, the sensor data comprising occupant data associated with the occupant of the seat and
a computer coupled to the sensor system, the computer comprising processing means for processing the sensor data including occupant data received from the occupant and configured to perform a predetermined action using the occupant data,
wherein the sensor system comprises
a first sensor coupled to the seat in a first location and configured to provide a first sensor signal and
a second sensor coupled to the seat in spaced-apart relation to the first sensor to provide a second sensor signal, the first and second sensors cooperate to sense at least one physiological attribute of the occupant through the at least one impeding barrier, and the first and second sensors are configured to communicate to the computer the first and second sensor signals,
wherein the computer is further configured to determine a reliability associated with each sensor signal, compare reliability of each sensor signal, and use one or more sensor signals having reliability greater than a predetermined value to provide at least the portion of the sensor data and
wherein the computer is further configured to compare the first and second sensor signals to provide derivative information included in the occupant data.

2. The occupant support system of claim 1, wherein the computer is further configured to calculate at least one of heart rate and respiration rate of the occupant using the occupant data before performing the predetermined action.

3. The occupant support system of claim 1, wherein the sensor system comprises a sensor coupled to the vehicle seat, configured to sense a physiological attribute of the occupant, and configured to provide at least a portion of the occupant data using the physiological attribute and wherein the sensor is located between a cushion of the seat and a trim layer of the seat, the sensor is further configured to sense the physiological attribute through the at least one impeding barrier comprising at least one of the trim layer and occupant's clothing.

4. The occupant support system of claim 3, wherein the sensor is one of an electrocardiogram (ECG) sensor, a pulse oxymetry sensor, a ballistocardiogram (BCG) sensor, and a galvanic skin response sensor.

5. The occupant support system of claim 1, wherein the computer is further configured to determine a blood pressure of the occupant using the derivative information and wherein the derivative information comprises a pulse transit time.

6. The occupant support system of claim 1, wherein the computer is further configured to receive occupant profile data associated with the occupant and combine the occupant profile data with the occupant data, and performing the predetermined action using the occupant data and the occupant profile data.

7. The occupant support system of claim 6, wherein the computer is configured to perform the predetermined action by determining an identity of the occupant using at least one of the occupant data and the occupant profile data.

8. The occupant support system of claim 6, wherein the computer is configured to perform the predetermined action by determining a driver capability assessment by analyzing respiration rate and processing rate changes over time.

9. The occupant support system of claim 6, wherein the computer is configured to perform the predetermined action by determining a driver stress level by analyzing heart rate variability.

10. The occupant support system of claim 6, wherein the computer is configured to perform the predetermined action by determining a health metric using at least one of the occupant data and the occupant profile data.

11. The occupant support system of claim 10, wherein the computer is configured to determine the health metric by calculating at least one of blood pressure, resting heart rate, and recovery time, the computer being further configured to receive factors including at least age, gender, weight, and combine the at least one of blood pressure, resting heart rate, and recovery time with factors to determine the health metric.

12. The occupant support system of claim 6, wherein the computer is configured to perform the predetermined action by determining a blood-flow metric by calculating blood volume data and using at least one of the occupant data and the occupant profile data.

13. The occupant support system of claim 6, wherein the computer is further configured to receive occupant profile data associated with the occupant, and to determine a baseline state associated with the occupant using the occupant profile data and wherein the computer is further configured to determine a current state of the occupant using the occupant data, compare the current state with the baseline state, and perform the predetermined action using the comparison of the current state and the baseline state.

14. The occupant support system of claim 13, wherein the computer is further configured to perform the predetermined action by adjusting occupant comfort via adjusting the seat to cause at least some of current state parameters to approximate at least some of baseline state parameters.

15. The occupant support system of claim 13, wherein the computer is further configured to perform the predetermined action by adjusting thermal comfort of the occupant by adjusting a thermal device in the seat to cause at least some of current state parameters to approximate at least some of baseline state parameters.

16. The occupant support system of claim 13, wherein the computer is further configured to perform the predetermined action by reducing stress parameters of the occupant by performing at least one of engaging a massage system coupled to the seat, adjusting an arrangement of the seat, and engaging a thermal device in the seat to cause at least some of current state parameters to approximate at least some of baseline state parameters.

17. The occupant support system of claim 13, wherein the computer is further configured to perform the predetermined action by increasing energy parameters of the occupant by performing at least one of engaging a massage system coupled to the seat, adjusting the seat to assume an upright arrangement, and engaging a thermal device included in the seat to adjust a seat temperature for the occupant.

18. The occupant support system of claim 1, wherein the computer is further configured to perform the predetermined action by determining a driver stress level by analyzing heart rate variability using occupant data and wherein the electronics system further includes a communication unit configured to transmit the driver stress level to a remote computer.

19. The occupant support system of claim 1, wherein the computer is further configured to perform the predetermined action by determining a driver stress level by analyzing heart rate variability using the occupant data and the sensor system further includes a location sensor configured to provide location data indicative of a location of the occupant and the computer is further configured to receive the location data and merge the location data with the occupant data to cause a location-related stress level of the occupant to be determined.

20. The occupant support system of claim 1, wherein the computer is further configured to determine physiological conditions of the occupant using the occupant data and store the physiological conditions over time to establish a collection of stored physiological conditions, wherein the electronics system further includes a communication unit coupled to the computer to receive commands from the computer and configured to communicate the collection of stored physiological conditions to a remote computer, and wherein the physiological conditions includes blood pressure and wherein the computer is further configured to calculate a trend over time of physiological conditions and determine if the trend of vital signs exceeds a predetermined threshold.

21. The occupant support system of claim 20, wherein the electronics system further includes a communication unit coupled to the computer to receive commands from the computer and configured to communicate the collection of physiological conditions to a remote computer when the computer determines the trend of physiological conditions exceeds a predetermined threshold.

22. The occupant support system of claim 1, further comprising one or more vehicle sensors coupled to the computer for producing one or more vehicle usage characteristic data, and wherein the computer is configured to process the sensor data including occupant data and vehicle usage characteristic data to perform the predetermined action and further comprising a communications device, coupled to the computer, wherein the computer is configured to transmit the occupant data via the communications device when the processed vehicle usage characteristic data determines a vehicle event has occurred.

23. The occupant support system of claim 1, wherein the computer is configured to determine the reliability of each signal by automatically adjusting a threshold for peak detection in each signal based on a height of a last detected peak and a leak decay multiplier.

* * * * *